US009737520B2

(12) United States Patent
Garcia Gil et al.

(10) Patent No.: US 9,737,520 B2
(45) Date of Patent: Aug. 22, 2017

(54) ACLIDINIUM FOR USE IN IMPROVING THE QUALITY OF SLEEP IN RESPIRATORY PATIENTS

(71) Applicant: Almirall, S.A., Barcelona (ES)

(72) Inventors: Maria Esther Garcia Gil, Barcelona (ES); Gonzalo De Miquel Serra, Barcelona (ES); Maria Jose Sala Peinado, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 15/161,531

(22) Filed: May 23, 2016

(65) Prior Publication Data

US 2016/0263091 A1   Sep. 15, 2016

Related U.S. Application Data

(63) Continuation of application No. 14/111,211, filed as application No. PCT/EP2012/056575 on Apr. 11, 2012, now abandoned.

(60) Provisional application No. 61/497,771, filed on Jun. 16, 2011.

(30) Foreign Application Priority Data

Apr. 15, 2011   (EP) .................................... 11382114

(51) Int. Cl.
*A61K 31/439* (2006.01)
*A61K 45/06* (2006.01)
*A61K 9/00* (2006.01)

(52) U.S. Cl.
CPC .......... *A61K 31/439* (2013.01); *A61K 9/0073* (2013.01); *A61K 9/0075* (2013.01); *A61K 45/06* (2013.01)

(58) Field of Classification Search
CPC .. A61K 31/439; A61K 2300/00; A61K 45/06; A61K 9/0073; A61K 9/0075
See application file for complete search history.

(56) References Cited

U.S. PATENT DOCUMENTS

| | | |
|---|---|---|
| 3,091,570 A | 5/1963 | Biel |
| 3,714,357 A | 1/1973 | Gueremy et al. |
| 4,224,332 A | 9/1980 | Gueremy et al. |
| 4,338,931 A | 7/1982 | Cavazza |
| 4,579,854 A | 4/1986 | Iwakuma et al. |
| 4,644,033 A | 2/1987 | Gnanou et al. |
| 4,675,326 A | 6/1987 | Amitai et al. |
| 4,843,074 A | 6/1989 | Rzeszotarski et al. |
| 4,855,290 A | 8/1989 | Fisher et al. |
| 5,201,308 A | 4/1993 | Newhouse |
| 5,254,330 A | 10/1993 | Ganderton et al. |
| 5,263,475 A | 11/1993 | Altermatt et al. |
| 5,290,539 A | 3/1994 | Marecki |
| 5,290,815 A | 3/1994 | Johnson et al. |
| 5,435,301 A | 7/1995 | Herold et al. |
| 5,507,281 A | 4/1996 | Kuhnel et al. |
| 5,569,447 A | 10/1996 | Lee et al. |
| 5,575,280 A | 11/1996 | Gupte et al. |
| 5,610,163 A | 3/1997 | Banholzer et al. |
| 5,617,845 A | 4/1997 | Poss et al. |
| 5,654,314 A | 8/1997 | Banholzer et al. |
| 5,676,930 A | 10/1997 | Jager et al. |
| 5,685,294 A | 11/1997 | Gupte et al. |
| 5,885,834 A | 3/1999 | Epstein |
| 5,962,505 A | 10/1999 | Bobrove et al. |
| 5,964,416 A | 10/1999 | Jaeger et al. |
| 6,150,415 A | 11/2000 | Hammock et al. |
| 6,299,861 B1 | 10/2001 | Banholzer et al. |
| 6,299,863 B1 | 10/2001 | Aberg et al. |
| 6,402,055 B1 | 6/2002 | Jaeger et al. |
| 6,410,563 B1 | 6/2002 | Deschenes et al. |
| 6,423,298 B2 | 7/2002 | McNamara et al. |
| 6,433,027 B1 | 8/2002 | Bozung et al. |
| 6,455,524 B1 | 9/2002 | Bozung et al. |
| 6,475,467 B1 | 11/2002 | Keller et al. |
| 6,481,435 B2 | 11/2002 | Hochrainer et al. |
| 6,497,373 B2 | 12/2002 | Jaeger et al. |
| 6,521,260 B1 | 2/2003 | Staniforth |
| 6,521,261 B2 | 2/2003 | Sherwood et al. |
| 6,537,524 B1 | 3/2003 | Hassan et al. |
| 6,608,054 B2 | 8/2003 | Meade et al. |
| 6,620,438 B2 | 9/2003 | Pairet et al. |
| 6,680,345 B2 | 1/2004 | Linz et al. |
| 6,686,346 B2 | 2/2004 | Nilsson et al. |
| 6,696,042 B2 | 2/2004 | Pairet et al. |
| 6,706,726 B2 | 3/2004 | Meissner et al. |
| 6,726,124 B2 | 4/2004 | Jaeger et al. |
| 6,749,015 B2 | 6/2004 | Moreau |

(Continued)

FOREIGN PATENT DOCUMENTS

| | | |
|---|---|---|
| AU | 2002257587 | 9/2002 |
| AU | 2003236784 B2 | 9/2003 |

(Continued)

OTHER PUBLICATIONS

U.S. Appl. No. 15/409,741, filed Jan. 19, 2017, Lamarca Casado et al.
U.S. Appl. No. 15/436,178, filed Feb. 17, 2017, Jarreta Fernandez et al.
Applicant-initiated Interview Summary dated Jan. 27, 2017, in U.S. Appl. No. 13/692,032.
Global Initiative for Chronic Obstructive Lung Disease, Global Strategy for the Diagnosis, Management, and Prevention of Chronic Obstructive Pulmonary Disease, 2006.

(Continued)

*Primary Examiner* — Savitha Rao
(74) *Attorney, Agent, or Firm* — Finnegan, Henderson, Farabow, Garrett & Dunner, LLP

(57) ABSTRACT

The present disclosure provides aclidinium or any of its stereoisomers or mixture of stereoisomers, or a pharmaceutically acceptable salt or solvate thereof, for improving the quality of sleep in respiratory patients.

15 Claims, No Drawings

(56) References Cited

U.S. PATENT DOCUMENTS

| | | |
|---|---|---|
| 6,750,226 B2 | 6/2004 | Forner et al. |
| 6,756,508 B2 | 6/2004 | Linz et al. |
| 6,814,953 B2 | 11/2004 | Banerjee et al. |
| 6,887,459 B1 | 5/2005 | Haeberlin |
| 6,890,517 B2 | 5/2005 | Drechsel et al. |
| 6,918,547 B2 | 7/2005 | Jaeger et al. |
| 6,919,325 B2 | 7/2005 | Linz et al. |
| 6,924,292 B2 | 8/2005 | Kawano et al. |
| 6,986,346 B2 | 1/2006 | Hochrainer et al. |
| 7,040,311 B2 | 5/2006 | Hochrainer et al. |
| 7,078,412 B2 | 7/2006 | Forner et al. |
| 7,104,470 B2 | 9/2006 | Jaeger et al. |
| 7,109,210 B2 | 9/2006 | Forner et al. |
| 7,122,558 B2 | 10/2006 | Prat Quinones et al. |
| 7,141,671 B2 | 11/2006 | Mammen et al. |
| 7,192,978 B2 | 3/2007 | Quinones et al. |
| 7,196,098 B2 | 3/2007 | Fernandez Forner et al. |
| 7,214,687 B2 | 5/2007 | Fernandez Forner et al. |
| RE39,820 E | 9/2007 | Banholzer et al. |
| 7,358,260 B2 | 4/2008 | Fernandez Forner et al. |
| 7,569,581 B2 | 8/2009 | Meissner et al. |
| 7,750,023 B2 | 7/2010 | Fernandez Forner et al. |
| 7,776,315 B2 | 8/2010 | Pairet et al. |
| 7,897,617 B2 | 3/2011 | Fernandez Forner et al. |
| 8,129,405 B2 | 3/2012 | Fernandez Forner et al. |
| 8,513,279 B2 | 8/2013 | Fernandez Forner et al. |
| 8,802,699 B2 | 8/2014 | Fernandez Forner et al. |
| 9,056,100 B2 | 6/2015 | Fernandez Forner et al. |
| 9,254,262 B2 | 2/2016 | Casado et al. |
| 9,333,195 B2 | 5/2016 | Fernandez Forner et al. |
| 2002/0025299 A1 | 2/2002 | Lewis et al. |
| 2002/0052312 A1 | 5/2002 | Reiss et al. |
| 2002/0115680 A1 | 8/2002 | Meissner et al. |
| 2002/0119991 A1 | 8/2002 | Meissner et al. |
| 2002/0122773 A1 | 9/2002 | Pairet et al. |
| 2002/0134538 A1 | 9/2002 | Moreau |
| 2002/0137764 A1 | 9/2002 | Drechsel et al. |
| 2002/0151541 A1 | 10/2002 | Pairet et al. |
| 2002/0151597 A1 | 10/2002 | Banerjee et al. |
| 2002/0179087 A1 | 12/2002 | Bozung et al. |
| 2002/0183292 A1 | 12/2002 | Pairet et al. |
| 2002/0189610 A1 | 12/2002 | Bozung et al. |
| 2002/0193392 A1 | 12/2002 | Schmelzer et al. |
| 2002/0193393 A1 | 12/2002 | Pairet et al. |
| 2003/0018019 A1 | 1/2003 | Meade et al. |
| 2003/0018061 A1 | 1/2003 | Ogawa et al. |
| 2003/0085480 A1 | 5/2003 | Yang |
| 2003/0096834 A1 | 5/2003 | Jenkins et al. |
| 2003/0130300 A1 | 7/2003 | Linz et al. |
| 2003/0139369 A1 | 7/2003 | Yeadon |
| 2003/0158196 A1 | 8/2003 | Jung et al. |
| 2003/0199539 A1 | 10/2003 | Germeyer et al. |
| 2003/0199545 A1 | 10/2003 | Grauert et al. |
| 2003/0203925 A1 | 10/2003 | Meade et al. |
| 2003/0216329 A1 | 11/2003 | Robinson et al. |
| 2004/0002548 A1 | 1/2004 | Bozung et al. |
| 2004/0024007 A1 | 2/2004 | Pairet et al. |
| 2004/0058950 A1 | 3/2004 | Meade et al. |
| 2004/0087617 A1 | 5/2004 | Meissner et al. |
| 2004/0151770 A1 | 8/2004 | Pairet et al. |
| 2004/0161386 A1 | 8/2004 | Pairet et al. |
| 2004/0167167 A1 | 8/2004 | Mammen et al. |
| 2004/0176338 A1 | 9/2004 | Pairet et al. |
| 2004/0184995 A1 | 9/2004 | Katsuma et al. |
| 2004/0192675 A1 | 9/2004 | Pairet et al. |
| 2004/0266869 A1 | 12/2004 | Montague et al. |
| 2005/0025718 A1 | 2/2005 | Meade et al. |
| 2005/0026886 A1 | 2/2005 | Meade et al. |
| 2005/0026887 A1 | 2/2005 | Meade et al. |
| 2005/0026948 A1 | 2/2005 | Meade et al. |
| 2005/0147564 A1 | 7/2005 | Drechsel et al. |
| 2005/0175547 A1 | 8/2005 | Maus et al. |
| 2005/0175548 A1 | 8/2005 | Goede et al. |
| 2005/0175549 A1 | 8/2005 | Goede et al. |
| 2005/0209272 A1 | 9/2005 | Fernandez Forner et al. |
| 2005/0244339 A1 | 11/2005 | Jauernig et al. |
| 2005/0256149 A1 | 11/2005 | Linz et al. |
| 2005/0267078 A1 | 12/2005 | Gras Escardo et al. |
| 2005/0267135 A1 | 12/2005 | Escardo et al. |
| 2005/0282875 A1 | 12/2005 | Prat Quinones et al. |
| 2005/0288266 A1 | 12/2005 | Gras Escardo et al. |
| 2006/0030579 A1 | 2/2006 | Park et al. |
| 2006/0057074 A1 | 3/2006 | Meade et al. |
| 2006/0079540 A1 | 4/2006 | Schmidt |
| 2006/0106055 A1 | 5/2006 | Fernandez Forner et al. |
| 2006/0106056 A1 | 5/2006 | Fernandez Forner et al. |
| 2006/0154934 A1 | 7/2006 | Escardo et al. |
| 2006/0189651 A1 | 8/2006 | Gras Escardo et al. |
| 2006/0196500 A1 | 9/2006 | Hochrainer et al. |
| 2006/0205702 A1 | 9/2006 | Escardo et al. |
| 2006/0252790 A1 | 11/2006 | Allen et al. |
| 2006/0285987 A1 | 12/2006 | Jaeger et al. |
| 2007/0128125 A1 | 6/2007 | Schmelzer et al. |
| 2008/0214600 A1 | 9/2008 | Fernandez Forner et al. |
| 2009/0088408 A1 | 4/2009 | Meade et al. |
| 2009/0299042 A1 | 12/2009 | Busquets Baque et al. |
| 2010/0234333 A1 | 9/2010 | Fernandez Forner et al. |
| 2010/0310477 A1 | 12/2010 | Pairet et al. |
| 2010/0330186 A1 | 12/2010 | Meade et al. |
| 2011/0020472 A1 | 1/2011 | Lamarca Casado et al. |
| 2011/0020454 A1 | 1/2011 | Lamarca Casado |
| 2011/0021477 A1 | 1/2011 | Gras Escardo et al. |
| 2011/0021478 A1 | 1/2011 | Gras Escardo et al. |
| 2011/0038806 A1 | 2/2011 | Meade et al. |
| 2011/0118223 A1 | 5/2011 | Forner et al. |
| 2011/0243924 A1 | 10/2011 | Beleta Supervia |
| 2012/0040943 A1 | 2/2012 | Gras Escardo et al. |
| 2012/0302532 A1 | 11/2012 | Gras Escardo et al. |
| 2012/0309727 A1 | 12/2012 | Gras Escardo et al. |
| 2013/0035319 A1 | 2/2013 | Gras Escardo et al. |
| 2013/0125884 A1 | 5/2013 | Lamarca Casado et al. |
| 2013/0189317 A1 | 7/2013 | Casado et al. |
| 2013/0196961 A1 | 8/2013 | Gras Escardo et al. |
| 2013/0252928 A1 | 9/2013 | Gras Escardo et al. |
| 2013/0310354 A1 | 11/2013 | Gras Escardo et al. |
| 2014/0094442 A1 | 4/2014 | Gras Escardo et al. |
| 2014/0100246 A1 | 4/2014 | Garcia Gil et al. |
| 2014/0296197 A1 | 10/2014 | Gras Escardo et al. |
| 2015/0080359 A1 | 3/2015 | Gras Escardo et al. |
| 2015/0093374 A1 | 4/2015 | Beleta Supervia |
| 2015/0118312 A1 | 4/2015 | Lamaraca Casado et al. |
| 2015/0246026 A1 | 9/2015 | Fernandez Forner et al. |
| 2015/0328194 A1 | 11/2015 | Jarreta Fernandez et al. |
| 2016/0296503 A1 | 10/2016 | Fernandez Forner et al. |
| 2016/0331733 A1 | 11/2016 | Jarreta Fernandez et al. |

FOREIGN PATENT DOCUMENTS

| | | |
|---|---|---|
| AU | 2003216921 | 10/2003 |
| AU | 2005202144 B2 | 6/2005 |
| CA | 2062854 | 9/1992 |
| CA | 2429012 | 5/2002 |
| CA | 2436540 | 5/2002 |
| CA | 2455167 | 1/2003 |
| CA | 2459493 | 3/2003 |
| CA | 2516467 | 9/2004 |
| DE | 10216333 | 10/2003 |
| EP | 0003445 | 8/1979 |
| EP | 0069715 | 1/1983 |
| EP | 0166294 | 1/1986 |
| EP | 0302699 A2 | 2/1989 |
| EP | 0418716 A1 | 3/1991 |
| EP | 0424021 A1 | 4/1991 |
| EP | 0424790 A1 | 5/1991 |
| EP | 0505321 | 9/1992 |
| EP | 0205247 B1 | 12/1992 |
| EP | 0424790 B1 | 8/1993 |
| EP | 0424021 B1 | 3/1994 |
| EP | 0418716 B1 | 4/1994 |
| EP | 0747355 | 12/1996 |
| EP | 0801067 A1 | 10/1997 |
| EP | 0603229 B1 | 6/1998 |
| EP | 0801067 B1 | 3/2003 |
| EP | 1087750 B1 | 11/2003 |

(56) References Cited

FOREIGN PATENT DOCUMENTS

| | | |
|---|---|---|
| EP | 1452179 | 9/2004 |
| EP | 1471919 B1 | 8/2005 |
| EP | 1651270 B1 | 3/2007 |
| EP | 1763369 B1 | 12/2008 |
| EP | 1763368 B1 | 3/2009 |
| EP | 2100599 | 9/2009 |
| ES | 2 165 768 | 3/2002 |
| ES | 2 206 021 | 5/2004 |
| ES | 2 239 546 | 9/2005 |
| FR | 2012964 | 3/1970 |
| GB | 1219606 | 1/1971 |
| GB | 2041763 | 9/1980 |
| GB | 2165159 | 4/1986 |
| GB | 2242134 | 9/1991 |
| GB | 2419819 | 5/2006 |
| HU | 178679 | 6/1982 |
| MX | PA03008045 | 12/2003 |
| WO | WO 87/07502 | 12/1987 |
| WO | WO 91/02558 | 3/1991 |
| WO | WO 91/04252 | 4/1991 |
| WO | WO 91/14468 | 10/1991 |
| WO | WO 92/00771 | 1/1992 |
| WO | WO 92/03175 | 3/1992 |
| WO | WO 92/04068 | 3/1992 |
| WO | WO 92/04345 | 3/1992 |
| WO | WO 92/04346 | 3/1992 |
| WO | WO 92/04928 | 4/1992 |
| WO | WO 92/09322 | 6/1992 |
| WO | WO 94/14492 | 7/1994 |
| WO | WO 95/24889 | 9/1995 |
| WO | WO 96/04346 | 2/1996 |
| WO | WO 96/19968 | 7/1996 |
| WO | WO 96/32150 | 10/1996 |
| WO | WO 97/00703 | 1/1997 |
| WO | WO 97/01337 | 1/1997 |
| WO | WO 97/12687 | 4/1997 |
| WO | WO 97/28801 | 8/1997 |
| WO | WO 97/34871 | 9/1997 |
| WO | WO 98/15280 | 4/1998 |
| WO | WO 99/51205 | 10/1999 |
| WO | WO 99/65464 | 12/1999 |
| WO | WO 00/05219 | 2/2000 |
| WO | WO 00/47200 | 8/2000 |
| WO | WO 01/04118 | 1/2001 |
| WO | WO 01/12167 | 2/2001 |
| WO | WO 01/50080 A2 | 7/2001 |
| WO | WO 01/50080 A3 | 7/2001 |
| WO | WO 01/57025 | 8/2001 |
| WO | WO 01/76601 A2 | 10/2001 |
| WO | WO 01/76601 A3 | 10/2001 |
| WO | WO 01/78736 | 10/2001 |
| WO | WO 01/78739 | 10/2001 |
| WO | WO 01/78741 | 10/2001 |
| WO | WO 01/78743 | 10/2001 |
| WO | WO 01/89491 | 11/2001 |
| WO | WO 02/09689 | 2/2002 |
| WO | WO 02/36106 | 5/2002 |
| WO | WO 02/38154 | 5/2002 |
| WO | WO 02/47667 | 6/2002 |
| WO | WO 02/051841 | 7/2002 |
| WO | WO 02/053564 A2 | 7/2002 |
| WO | WO 02/053564 A3 | 7/2002 |
| WO | WO 02/060532 | 8/2002 |
| WO | WO 02/060533 A2 | 8/2002 |
| WO | WO 02/060533 A3 | 8/2002 |
| WO | WO 02/066422 | 8/2002 |
| WO | WO 02/096423 A2 | 12/2002 |
| WO | WO 02/096423 A3 | 12/2002 |
| WO | WO 02/096463 | 12/2002 |
| WO | WO 03/000241 | 1/2003 |
| WO | WO 03/000289 | 1/2003 |
| WO | WO 03/000325 | 1/2003 |
| WO | WO 03/011274 A2 | 2/2003 |
| WO | WO 03/011274 A3 | 2/2003 |
| WO | WO 03/024452 | 3/2003 |
| WO | WO 03/042160 | 5/2003 |
| WO | WO 03/061742 | 7/2003 |
| WO | WO 03/066063 | 8/2003 |
| WO | WO 03/066063 A1 | 9/2003 |
| WO | WO 03/074025 A2 | 9/2003 |
| WO | WO 03/074025 A3 | 9/2003 |
| WO | WO 03/087094 A2 | 10/2003 |
| WO | WO 03/087094 A3 | 10/2003 |
| WO | WO 03/097098 | 11/2003 |
| WO | WO 03/097613 | 11/2003 |
| WO | WO 2004/005285 | 1/2004 |
| WO | WO 2004/043966 | 5/2004 |
| WO | WO 2004/058729 | 7/2004 |
| WO | WO 2004/074267 | 9/2004 |
| WO | WO 2004/074276 | 9/2004 |
| WO | WO 2004/074276 A1 | 9/2004 |
| WO | WO 2004/084896 | 10/2004 |
| WO | WO 2004/084897 | 10/2004 |
| WO | WO 2005/013993 | 2/2005 |
| WO | WO 2005/013994 | 2/2005 |
| WO | WO 2005/014005 | 2/2005 |
| WO | WO 2005/014044 A1 | 2/2005 |
| WO | WO 2005/049581 | 6/2005 |
| WO | WO 2005/090342 | 9/2005 |
| WO | WO 2005/097126 | 10/2005 |
| WO | WO 2005/115462 | 12/2005 |
| WO | WO 2005/115463 | 12/2005 |
| WO | WO 2005/115464 | 12/2005 |
| WO | WO 2005/115465 A1 | 12/2005 |
| WO | WO 2005/115466 | 12/2005 |
| WO | WO 2005/115467 | 12/2005 |
| WO | WO 2006/105401 | 10/2006 |
| WO | WO 2008/009397 | 1/2008 |
| WO | WO 2008/096121 | 8/2008 |
| WO | WO 2008/102128 | 8/2008 |
| WO | WO 2009/112273 A2 | 9/2009 |
| WO | WO 2009/112273 A3 | 9/2009 |
| WO | WO 2009/112274 A2 | 9/2009 |
| WO | WO 2009/112274 A3 | 9/2009 |
| WO | WO 2013/175013 A1 | 11/2013 |
| WO | WO 2014/095663 | 6/2014 |

OTHER PUBLICATIONS

Jones et al., "Efficacy and safety of once-daily aclidinium in chronic obstructive pulmonary disease," Respiratory Research, 2011; 12: 55 (10 pages).

Jones et al., "Efficacy and safety of twice-daily aclidinium bromide in COPD patients: the ATTAIN study," Eur. Respir. J., 2012; 40(4): 830-836.

Kerwin, E., "Efficacy and Safety of a 12-week Treatment with Twice-daily Acdlinium Bromide in COPD Patients (ACCORD COPD I)," COPD: Journal of Chronic Obstructive Pulmonary Disease, 2012; 9(2): 90-101.

Magnussen, H. et al., "The effect of aclidinium bromide 400 μg on sleep quality in COPD: A pilot study," European Respiratory Journal, 2016; 48: PA4051 (Abstract).

Magnussen, H. et al., "The effect of aclidinium bromide 400 μg on sleep quality in COPD: A pilot study," European Respiratory Society Congress, London, UK, Sep. 3-7, 2016 (Poster).

Miller, J. et al., "Standardisation of spirometry," Eur Respir J, 2005; 26: 319-338. Murray, J. et al., Eds., Textbook of Respiratory Medicine, Third Edition, W.B. Saunders Company, Philadelphia, 2000, ISBN 0-7216-7711-8, Chapters 11 and 38, pp. 267-296 and 1187-1245.

Office Action dated Feb. 9, 2017, in U.S. Appl. No. 13/692,032, (18 pages).

Office Action dated Feb. 15, 2017, in U.S. Appl. No. 14/561,857, (14 pages).

Parfitt, K., Ed., Martindale: The Complete Drug Reference, Thirty-Second Edition, 1999, 7457-75 (cited in IDS filed on Oct. 17, 2016 but different page numbers—pp. 745-775.

Reynolds, J., Ed., Martindale: The Extra Pharmacopoeia, Twenty-ninth Edition, 1998, 522.

Spiriva Prescribing Information published 2004.

(56) References Cited

OTHER PUBLICATIONS

U.S. Appl. No. 12/787,772 Suggestion for Interference dated Nov. 23, 2010, 15 pages.
U.S. Appl. No. 12/875,601, Appeal Brief, filed Oct. 6, 2016, 35 pages.
U.S. Appl. No. 12/875,601 Final Office Action dated Sep. 24, 2015, 29 pages.
U.S. Appl. No. 12/875,601 Examiner's Answer to Appeal Brief dated Dec. 2016, 16 pages.
U.S. Appl. No. 14/305,701 Non-Final Office Action dated May 16, 2016, 17 pages.
U.S. Appl. No. 14/305,701 Response to Non-Final Office Action dated Nov. 16, 2016, 126 pages.
U.S. Appl. No. 15/019,009 Non-Final Office Action dated Oct. 12, 2016, 26 pages.
U.S. Appl. No. 15/095,036 Non-Final Office Action dated Aug. 2, 2016, 9 pages.
U.S. Appl. No. 10/047,464, filed Jan. 14, 2002, Dolors Fernandez Forner et al.
U.S. Appl. No. 10/740,264, filed Dec. 17, 2003, Maria Dolors Fernandez Forner et al.
U.S. Appl. No. 10/891,552, filed Jul. 15, 2004, Meade et al.
U.S. Appl. No. 10/892,033, filed Jul. 15, 2004, Christopher John Montague Meade et al.
U.S. Appl. No. 11/116,777, filed Apr. 28, 2005, Maria Dolors Fernandez Forner et al.
U.S. Appl. No. 11/141,169, filed May 31, 2005, Jordi Gras Escardo et al.
U.S. Appl. No. 11/141,427, filed May 31, 2005, Jordi Gras Escardo et al.
U.S. Appl. No. 11/141,428, filed May 31, 2005, Maria Dolors Fernandez Forner et al.
U.S. Appl. No. 11/324,919, filed Jan. 3, 2006, Maria Dolors Fernandez Forner et al.
U.S. Appl. No. 11/325,059, filed Jan. 3, 2006, Maria Dolors Fernandez Forner et al.
U.S. Appl. No. 11/636,181, filed Dec. 8, 2006, Maria Dolors Fernandez Forner et al.
U.S. Appl. No. 12/074,929, filed Mar. 7, 2008, Maria Dolors Fernandez Forner et al.
U.S. Appl. No. 12/374,185, filed Feb. 11, 2009, Nuria Busquets Baque et al.
U.S. Appl. No. 12/528,267, filed Aug. 21, 2009, Jorge Beleta Supervia.
U.S. Appl. No. 12/787,772, filed May 26, 2010, Maria Dolors Fernandez Forner et al.
U.S. Appl. No. 12/875,601, filed Sep. 3, 2010, Meade et al.
U.S. Appl. No. 12/912,145, filed Oct. 26, 2010, Meade et al.
U.S. Appl. No. 12/921,892, filed Sep. 10, 2010, Rosa Lamarca Casado.
U.S. Appl. No. 12/921,921, filed Oct. 5, 2010, Rosa Lamarca Casado et al.
U.S. Appl. No. 13/011,131, filed Jan. 21, 2011, Maria Dolors Fernandez Forner et al.
U.S. Appl. No. 13/672,893, filed Nov. 9, 2012, Rosa Lamarca Casado et al.
U.S. Appl. No. 13/692,032, filed Dec. 3, 2012, Lamarca Casado et al.
U.S. Appl. No. 13/862,370, filed Apr. 2013, Gras Escardo et al.
U.S. Appl. No. 14/111,211, filed Oct. 11, 2013, Garcia Gill et al.
U.S. Appl. No. 14/403,220, filed Nov. 24, 2014, Lamarca Casado et al.
U.S. Appl. No. 14/471,819, filed Aug. 28, 2014, Gras Escardo et al.
U.S. Appl. No. 14/549,347, filed Nov. 20, 2014, Gras Escardo et al.
U.S. Appl. No. 14/561,857, filed Dec. 5, 2014, Beleta Supervia.
U.S. Appl. No. 14/652,817, filed Jun. 17, 2015, Diana Jarreta Fernandez et al.
U.S. Appl. No. 14/712,866, filed May 14, 2015, Fernandez Forner et al.
U.S. Appl. No. 14/795,194, filed Jul. 2015, Gras Escardo et al.
U.S. Appl. No. 14/920,519, filed Oct. 22, 2015, Gras Escardo et al.
U.S. Appl. No. 15/019,009, filed Feb. 9, 2016, Dolors Fernandez Forner et al.
U.S. Appl. No. 15/080,475, filed Mar. 24, 2016.
U.S. Appl. No. 15/095,036, filed Apr. 9, 2016.
U.S. Appl. No. 15/159,643, filed May 19, 2016.
U.S. Appl. No. 15/218,391, filed Jul. 25, 2016, Jarreta Fernandez et al.
6001 chemical abstracts, Columbus, OH, US, vol. 104(19). XP-002128290, p. 659 (1985).
ABPI Medicines Compendium 2003: Data Sheets for Duovent Autohaler, Duovent Inhaler, Duovent UDVs, pp. 643-646, ISBN 0 907102 20 4.
ABPI Medicines Compendium 2003: Data Sheets for Spiriva, pp. 1999-2001, ISBN 0 907102 20 4.
ABPI Medicines Compendium 2003: Data Sheets for Atrovent Aerocaps, Atrovent Autohaler, Atrovent Forte MA, Atrovent Metered Dose Inhaler, Atrovent UDVs, pp. 151-155, ISBN 0 907102 20 4.
ABPI Medicines Compendium 2003: Data Sheets for Combivent Metered Aerosol, Combivent UDVs, pp. 439-441, ISBN 0 907102 20 4.
ABPI Medicines Compendium 2003: Data Sheets for Oxivent Autohaler, Oxivalent Inhaler, pp. 1615-1616, ISBN 0 907102 20 4.
Alabaster, V., "Discovery and Development or Selective M3 Antagonists for Clinical Use," Life Sciences, 1997,60 (13/14), 1053-1060.
Alabaster, "Discovery & Development of Selective M3 Antagonists for Clinical Use"; Life Sciences, vol. 60, No. 13114, 1997, I page—Abstract Only.
Amakye, ., et al., "Pharmacokinetics (PK) and Pharmacodynamics (PO) of SCI0-469, A P38 Gamma Map Kinase Inhibitor," Clinical Pharmacology and Therapeutics, 2004, 5 (2), p. 54: Abst PII-7.
Andersson, P, Presentation labeled "Aclidinium bromide, a novel inhaled long-acting anticholinergic", presented Sep. 17, 2007, 16 pages.
Appeal Brief in U.S. Appl. No. 10/892,033 dated Aug. 30, 2010.
Atkins, P J. et al., "Dry Powder Inhalers: An Overview", Respiratory Care, vol. 50, No. 10, Oct. 2005, pp. 1304-1312.
Atrovent® (ipratropium bromide) Inhalation Solution Prescribing Information, Boehringer Ingelheim International GmbH 830885-R, Revised Oct. 1998.
Atrovent® Aerosol Prescribing Information, Boehringer Ingelheim International GmbH 10001403US/1, 10001403/01, Revised Mar. 27, 2002.
Auerbach, D. et al., "Routine Nebulized Ipratropium and Albuterol Together are Better Than Either Alone in COPD," The COMBIVENT Inhalation Solution Study Group, Chest, 1997, 112, 1514-1521.
Avdeyev, S.M., "Anticholinergic Preparations in Obstructive Pulmonary Diseases", Atmosphera, 2002, No. I, pp. 20-23. (English translation also attached).
Ayres, JG et al. Thorax 52(Supp 1): S1-S21 (1997).
Bach, P. et al., "Management of Acute Exacerbations of Chronic Obstructive Pulmonary Disease: A Summary and Appraisal of Published Evidence," Annals of Internal Medicine, 2001, 134 (7), 600-620.
Baeumer, et al., "Cilomilast, an orally active phosphodiesterase 4 inhibitor for the treatment of COPD," Expert Rev. Clin. Immunol., 1(1): 27-36 (2005).
Banner, K. et al., "The Effect of Selective Phosphodiesterase 3 and 4 Isoenzyme Inhibitors and Established Anti-Asthma Drugs on Inflammatory Cell Activation," British Journal of Pharmacology, 1996, 119, 1255-1261.
Barnes P., Ed., Managing Chronic Pulmonary Disease, Second Edition, Science Press Ltd, London, 2001, ISBN 1-85873-932-2, Chapter 2: Clinical Features, pp. 28-31, 35; Chapter 3: Drugs Used in the Management of COPD, pp. 40-43; Chapter 4: Management of COPD, pp. 57-62, 66; Chapter 5: Future Trends in Therapy, pp. 73-75.
Barnes, P. et al., "COPD: Current Therapeutic Interventions and Future Approaches," European Respiratory Journal, 2005, 25 (6), 1084-1106.

(56) References Cited

OTHER PUBLICATIONS

Barnes, P. et al., "Prospects for New Drugs for Chronic Obstructive Pulmonary Disease," Lancet 2004, 364, 985-996.
Barnes, P. et al., "The Effect of Platelet Activating Factor on Pulmonary-Adrenoceptors," British Journal of Pharmacology, 1987, 90, 709-715.
Barnes, P. et al., Eds., Asthma and COPD, Basic Mechanisms and Clinical Management, Academic Press, Amsterdam, 2002, ISBN 0-12-079028-9, pp. 523, 530-531, 731.
Barnes, P. et al., Eds., Asthma, vol. 2, Lippincott-Raven, Philadelphia, 1997, ISBN 0-39751682-7, Chapter 142: Compliance by H. Mawhinney et al., pp. 2099-2113.
Barnes, P. et al., Eds., The Role of Anticholinergics in Chronic Obstructive Pulmonary Disease and Chronic Asthma, Gardiner-Caldwell Communications Limited, UK, 1997, ISBN 1 896729 14 X, Foreword and Chapter 9: Anticholinergics and P2-Agonists: Efficacy, Safety and Combination Therapy inn Chronic Pulmonary Disease by S.I,. Rennard et al., pp. 137-144.
Barnes, P., "Advances in Chronic Obstructive Pulmonary Disease," Ordinary Meeting, Jan. 13, 2003, pp. 41-51.
Barnes, P., "Chronic Obstructive Pulmonary Disease 12: New Treatments for COPD," Thorax, 2003, 58(9), 803-808.
Barnes, P., "COPD: Is There Light at the End of the Tunnel?," Current Opinion in Pharmacology, 2004, 4, 263-272.
Barnes, P., "Future Advances in COPD Therapy," Respiration, 2001, 68, 441-448.
Barnes, P., "New Drugs for Asthma," Nature Reviews, Drug Discovery, 2004, 3, 831-844.
Barnes, P., "The Role of Anticholinergics in Chronic Obstructive Pulmonary Disease," American Journal of Medicine, 2004, 117 (12A), 24S-32S.
Beasley, R. et al., "Withdrawal of Fenoterol and the End of the New Zealand Asthma Mortality Epidemic," International Archives of Allergy and Immunology, 1995, 107, 325-327.
Beeh, K., et al., "Aclidinium Bromide Improves Exercise Endurance and Dynamic Hyperinflammation and Decreases Exertional Dyspnoea in Patients With Moderate-To-Severe COPD," Am J Respir Crit Care Med, 2013; 187: A2430.
Berenbaum, M., "Synergy, Additivism and Antagonism in Immunosuppression, A Critical Review," Clinical and Experimental Immunology, 1977, 28, 1-18.
Berenbaum, M., "What is Synergy?," Pharmacological Reviews, 1989, 41, 93-141 and Errata, p. 422.
Berkow, R. et al., Eds., The Merck Manual of Diagnosis and Therapy, Sixteenth Edition, 1992, Foreword and Chapter 34, "Airways Obstruction Asthma," pp. 646-657.
Boehringer Ingelheim International GmbH, European Patent No. 1 651 270 B1 as proposed to be amended, 20 pages, first submitted to the U.S. Patent and Trademark Office in U.S. Appl. No. 12/070,298 on Oct. 19, 2009.
Bone, R. et al., "In Chronic Obstructive Pulmonary Disease, A Combination of Ipratropium and Albuterol is More Effective that Either Agent Alone: An 85-Day Multicenter Trial," COMBIVENT Inhalation Aerosol Study Group, Chest, 1994, 105, 1411-1419.
Boswell-Smith et al., "Are phosphodiesterase 4 inhibitors just more theophylline?" J. Allergy Clin. Immunology, 117(6): 1237-1243 (Jun. 2006).
Boulet, L P et al., "Canadian asthma consensus report, 1999" CMAJ/JAMC, vol. 161 (11 Suppl), 1999, pp. s1, s44-s50.
Boyd et al., "An evaluation of salmeterol in the treatment of chronic obstructive pulmonary disease (COPD)" Eur Respir J. 1997; 10:815-821.
Braunwald, E. et al., Eds., Harrison's 15th Edition, Principles of Internal Medicine, vol. 2, McGraw-Hill, New York, 2001, ISBN 0-07-007272-4, Section Titled: Chronic Bronchitis, Emphysema, and Airways Obstruction by E.G. Honig et al., pp. 1491, 1495-1496.
Brittain, H G., "What is the "correct" method to use for particle-size determination?"; Pharmaceutical Technology, Jul. 2001, pp. 96, 98.
British National Formulary 45, Mar. 2003, ISBN 0 7279 1772 2, Chapter 3: Respiratory System, pp. 131-165.

British Thoracic Society, "BTS Guidelines for the Management of Chronic Obstructive Pulmonary Disease," The COPD Guidelines Group of the Standards of Care Committee of the BTS, Thorax, 1997, 52, Supplement 5, SI-S28.
British Thoracic Society, "BTS Guidelines for the Management of Chronic Obstructive Pulmonary Disease," The COPD Guidelines Group of the Standards of Care Committee of the BTS, Thorax, 1997, 52, Supplement 5, S1-S28, retrieved Mar. 13, 2014, from thorax.bmj.com.
British Thoracic Society, British Guideline on the Management of Asthma, Thorax, 2003, 58, Supplement I, iI-i94.
Brodde, 0-E., "1- and 2-Adrenoceptors in the Human Heart: Properties, Function, and Alterations in Chronic Heart Failure," Pharmacological Reviews, 1991, 43 (2), 203-242.
Bryant, D., "Nebulized Ipratropium Bromide in the Treatment of Acute Asthma," Chest, 1985.
Buhl, R. et al., "Future Directions in the Pharmacologic Therapy of Chronic Obstructive Pulmonary Disease," Proceedings of the American Thoracic Society, 2005, 2 (1), 83-93.
Burtner, R. et al., "Antispasmodics II. Basic Esters of Some Polynuclear Carboxylic Acids," J. Am. Chem. Soc. 65: 1582-1585 (1943).
Calverley, P.M.A. et al., "Salmeterol and Fluticason Propionate and Survival in Chronic Obstructive Pulmonary Disease," New England Journal of Medicine, 2007, 356 (8), 775-789.
Calverley, P.M.A., "Effect of tiotropium bromide on circadian variation in airflow limitation in chronic obstructive pulmonary disease," Thorax, 58: 855-860; (2003).
Calverley, P.M.A., Ed., Chronic Obstructive Pulmonary Disease, Chapman and Hall, London, 1995, ISBN 0 412 46450, Chapter 16: Bronchodilators: Basic Pharmacology by P.J. Barnes, pp. 391 and 398-401.
Cazzola, M. et al., "The Functional Impact of Adding Salmeterol and Tiotropium in Patients with Stable COPD," Respiratory Medicine, 2004, 98, 1214-1221.
Cazzola, M. et al., "The Pharmacodynamic Effects of Single Inhaled Doses of Formoterol, Tiotropium and Their Combination in Patients with COPD," Pulmonary Pharmacology & Therapeutics, 2004,17,35-39.
Chanez, P. et al., "Once-Daily Administration of Aclidinium Bromide, A Novel, Long-Acting Anticholinergic: A Phase II, Dose Finding Study," Published as Poster Presentation at European Respiratory Society Annual Congress in Berlin, Germany, 2008, 2 pages.
Chanez, P. et al., "Once-Daily Administration of Aclidinium Bromide, A Novel, Long-Acting Anticholinergic: A Phase II, Dose Finding Study," Eur. Respir. J., vol. 32, 2008, p. 476s, Abstract 2736.
Christensen et al., "1,4-Cyclohexanecarboxylates: Potent and Selective Inhibitors of Phosphodiesterase 4 for the Treatment of Asthma," J. Med. Chem. 41:821-835 (1998).
Chrystn, H. et al., "The Genuair® inhaler: a novel, multidose dry power inhaler," International Journal of Clinical Practice, vol. 66, No. 3, pp. 309-317 (2012).
Chuchalin A.G. et al: "Clinical Equivalence Trial on Budesonide Delivered either by the Novolizer Multidose Dry Power Inhaler or the Turbuhaler in Asthmatic Patients" Respiration; 69: 502-508 (2002).
Chung, K., "Phosphodiesterase Inhibitors in Airways Disease," European Journal of Pharmacology, 2006, 533, 110-117.
Clarkson, E. et al., "Binding and Active Transport of Large Analogues of Acetylcholine by Cholinergic Synaptic Vesicles In Vitro," Journal of Neurochemistry, 1992, 59, 695-700.
Cohen, VI et al., "Synthesis and Receptor Affinities for New 3-Cuinuclidinyl a-Heteroaryl-a-aryl-a-Hydroxyacetates," J. Pharm. Sciences, 81: 326-329 (1992).
COMBIVENT Advertisement in American Journal of Respiratory and Critical Care Medicine, Feb. 1, 2003, 167 (3), 4 pages.
COMBIVENT Advertisement in ATS 2003 Seattle 99th International Conference Final Program, May 16-21, 2003, 4 pages.
COMBIVENT, Inhalation Aerosol Prescribing Information, Boehringer Ingelheim International GmbH, 10000291/03, revised Sep. 2001.

(56) References Cited

OTHER PUBLICATIONS

COMBIVENT® Advertisement in Chest, 2003, 123 (6), 4 pages.
Costain, D. et al., "Guidelines for Management of Asthma in Adults: I-Chronic Persistent Asthma," Br. Med. J. 301: 651-653 (1990).
Cui, X. "Sleep disorder of patients suffering from chronic obstructive pulmonary disease and nursing countermeasures thereof," China Practical Medicine, 32(3): 141-142: 2008, translation included.
Davis, MA et al. "New Psychotropic Agents VI, Basic Esters of 5-Hydroxydibenzo[a,d]cycloheptadiene-5-carboxylic acid," J. Med. Chem 6: 513-51 (1963).
Davis, MA et al., "Anticonvulsants I. Dibenzo[a,d]cycloheptadiene-5-carboxamide and Related Compounds," J. Med. Chem 7: 88-94 (1964)).
Dent, et al., "Effectis of a Selective PDE4 Inhibitor, D-22888, on Human Airways and Eosinophils in vitro and Late Phase Allergic Pulmonary Eosinophilia in Guinea Pigs," Pulmonary Pharma & Thera. 11:13-21 (1998).
Disse, B. et al., "BA 679 BR, A Novel Long-Acting Anticholinergic Bronchodilator," Life Sciences, 1993,52,537-544.
Disse, B., "Antimuscarinic Treatment for Lung Disease, From Research to Clinical Practice," Life Sciences, 2001, 68, 2557-2564.
Dompeling, E. et al., "Slowing the Deterioration of Asthma and Chronic Obstructive Pulmonary Disease Observed During Bronchodilator Therapy by Adding Inhaled Corticosteroids," Annals of Internal Medicine, 1993, 118, 770-778.
Donohue, "Minimal clinically important differences in COPD lung function," Journal of Chronic Obstructive Pulmonary Disease, vol. 2, No. 1, pp. 111-124 (2005) (Abstract).
Down, et al., "Clinical Pharmacology of Cilmilast," Clin. Pharmacokinet, 45(3): 217-233 (2006), abstract.
Drug Information Display, "Generic Name: Atropine-Oral, Brand Name(s): Sal-Tropine," obtained from www.medicinenet.com, p. 1 of 3, as of Nov. 4, 2008.
Durham, M. "Tiotropium (Spiriva): a once-daily inhaled anticholinergic medication for chronic obstructive pulmonary disease," BUMC Proceedings, 17: 366-373 (2004).
Dyke, H. et al., "Update on the Therapeutic Potential ofPDE4 Inhibitors," Expert Opinion on Investigational Drugs, 2002, 11 (1), 1-13.
Easton, P. et al., "A Comparison of the Bronchodilating Effects of a Beta-2 Andrenergic Agent (Albuterol) and an Anticholinergic Agent (Ipratropium Bromide), Given by Aerosol Alone or in a Sequence," New England Journal of Medicine, 1986, 315 (12), 735-739.
Eglen, R. et al., "Muscarinic Receptor Subtypes and Smooth Muscle Function," Pharmacological Reviews, 1996, 48 (4), 531-565.
Eglen, RM et al., "Muscarinic Receptor Subtypes: Pharmacology and Therapeutic Potential," DN & P, 10(8): 462-469 (Oct. 1997).
Emea, "Note for Guidance on Dose Response Information to Support Drug Registration," ICH Topic E 4. 1994. CPMP/ICH/378/95.
English Abstract for Romain, O. et al., "Actualites Pharmaceutiques," (2006) 1596-1598, 13(12), XP027997707, ISSN: 0929-693X, DOI:10.1016/J.ARCPED.2006.09.019, Archives De Pediatrie, Elsevier, Paris, FR.
English language abstract for DE10216333, retrieved from the European Patent Office website on Mar. 28, 2013, 2 pages.
English Translation—Instructions for Medicine, The Merck Manual, M., "MIR", 1997, vol. 2, p. 693.
English Translation—Mikhailov, I.B., Desk Book of the Physician for clinical pharmacology, St. Petersburg, 2001, pp. 424-425, 428, 439-440.
English-language abstract for HU 178679, retrieved from the European Patent Office website on Nov. 21, 2003, 1 page.
English-language abstract for WO 2004/074267.
English-language abstract for WO 2003/024452
English-language abstract for WO 2003/061742.
English-language Machine Translation of Grob, CA et al. "Die Synthese von 4-Brom- und 4-Hydroxy0Chinuclidin," Helv. Chim. Acta 41: 1184-1191 (1958).
English-language Machine Translation of Konzett, H. et al. "Versuchsanordnung zu Untersuchungnen an der Bronchialmuskulatur," Arch. Exp. Path. Pharmacol. 195: 71-74 (1940).
English-language Machine Translation of Rigaudy, J et al. "Cetones Derivees du Dibzeno [a,d]cycloheptadiene. La Dibenzo-2,3-6,7 Cycloheptadienedione-4,5" Bull. Soc. Chim. France, 638-643 (1959).
English-language translation of Official Action issued Mar. 25, 2009, in Russian Patent Application No. 2006147250, 3 pages.
English-language translation of p. 1554 of Medical Dictionary, Edited by Ishiyaku Shuppan KK, 2001, 1 page.
English-language translation of p. 96, Table 3-7 Introduction to Pharmacology, 2003, 1 page.
English-language translation of pp. 20, 23 of Pharmacology Manual, Edited by KK Nanzando, 2002, 2 pages.
EP2265258 Office Action dated Apr. 24, 2013, Application No. 09 720 773.2-1455.
EPO Application No. 04763322.7-2123, Third Party Observations dated Jul. 8, 2008.
Etzler, F M. et al., "Particle size analysis; a comparative study of various methods", Part. Part. Syst. Charact., vol. 12, Oct. 1995; pp. 217-224.
European Medicines Agency Assessment Report—Brimica Genuair, Sep. 25, 2014, pp. 1-136.
European Medicines Agency Committee for Medicinal Products for Human Use (CHMP), Guideline on the Pharmaceutical Quality of Inhalation and Nasal Products (2006).
European No. 1 763 369, Notice of Opposition dated Sep. 15, 2009, and English-language translation (27 pages total, 16 pages translation).
European Patent Application No. 05750538.0-2107 Reply to Communication, dated Mar. 11, 2008, 3 pages.
European Patent Application No. 09729773.2 Communication pursuant to Article 94(3) EPC dated Apr. 24, 2013, 9 pages.
European Patent No. 1651270, Decision Revoking the European Patent, dated May 18, 2010, 12 pages.
European Patent No. 1651270, Grounds of Opposition by Laboratories Almirall, S.A., dated Dec. 21, 2007, 12 pages.
European Patent No. 1651270, Minutes of the Oral Proceedings before the Opposition Division on Mar. 17, 2010, 7 pages.
European Patent No. 1651270, Opponent's Reply to the Patentee's Grounds of Appeal dated Feb. 2011, 48 pages.
European Patent No. 1651270, Opponent's Response to Summons to Oral Proceedings, dated Jan. 14, 2010, 13 pages.
European Patent No. 1651270, Patentee's Appeal Requests, dated Sep. 28, 2010, 24 pages.
European Patent No. 1651270, Patentee's Rebuttal to Grounds of Opposition, dated May 30, 2008, 13 pages.
European Patent No. 1651270, Patentee's Response to Summons to Attend Oral Proceedings dated Jul. 30, 2009, and Opponent's Submission of May 22, 2009, dated Oct. 1, 2009, 18 pages.
European Patent No. 1651270, Patentee's Response, Feb. 18, 2010, 7 pages.
European Patent No. 1651270, Patentee's Submissions of Oral Proceedings, dated Jan. 15, 2010, 10 pages.
European Patent No. 1651270, Reply to Submission from Patentee dated May 30, 2008, dated May 2009, 39 pages.
European Patent No. 1763368, Opposition to European Patent No. 1763368, Patentee's Experimental Report 1, 1 page, submitted to the European Patent Office Jul. 28, 2010.
European Patent No. 1763368, Opposition to European Patent No. 1763368, Patentee's Experimental Report 2, 1 page, submitted to the European Patent Office Jul. 28, 2010.
European Patent No. 1763368, Opposition to European Patent No. 1763368, Patentee's Experimental Report 3, 8 pages, submitted to the European Patent Office Jul. 28, 2010.
European Patent No. 1763368, Opposition to European Patent No. 1763368, Patentee's Experimental Report 4, 6 pages, submitted to the European Patent Office Jul. 28, 2010.

(56) References Cited

OTHER PUBLICATIONS

European Patent No. 1763368, Reply to Oppositions Filed against European Patent No. 1763368, dated Jul. 26, 2010, 39 pages.
European Patent No. 1763368, Statement of Opposition by Boehringer Ingelheim Pharma GmbH & Co. KG, dated Dec. 2, 2009, 8 pages (in German).
European Patent No. 1763368, Statement of Opposition by Norton Healthcare Ltd, dated Nov. 9, 2009, 18 pages.
European Pharmacopeia 7.0, pp. 274-285 (2010).
Fenton, C. et al., "Novolizer: A Multidose Dry Powder Inhaler", Drugs, vol. 63, No. 22, 2003, 2437-2445.
Fitzgerald, M. F. et al., "Emerging trends in the therapy of COPD: bronchodilators as mono- and combination therapies," Drug Discovery Today, 12(11/12): 472-478 (2007).
Food and Drug Administration, Center for Drug Evaluation and Research, "Clinical Pharmacology and Biopharmaceutics Review(s)—NDA No. 21-077", 107 pages. Available from: http://www.acessdata.fda.gov/drugsatfda_docs/nda/2000/21077_Advair%20Diskus_biopharmr.pdf.
Food and Drug Administration, Center for Drug Evaluation and Research, "Pharmacology Review(s)—NDA No. 20-831", 151 pages. Available from: http://www.acessdata.fda.gov/drugsatfda_docs/nda/2001/20831_Foradil_phrmr_P1.pdf.
Food and Drug Administration, Center for Drug Evaluation and Research, "Pharmacology Review(s)—NDA No. 20-833", 8 pages. Available from: http://www.acessdata.fda.gov/drugsatfda_docs/nda/2000/20-833_Flovent_Pharmr.pdf.
Foradil Aerolizer (formoterol fumarate) production information from Merck Product Services, downloaded May 3, 2012, from http://www.merckservices.com/portal/site/merckproductservices/foradil/zQzWTzPzsvlzEz4.
Foye, et al., Principles of Medicinal Chemistry, 4th Edition, pp. 338-340 (1995).
Frijlink, HW et al., "Dry powder inhalers for pulmonary drug delivery", Expert Opinion Drug Delivery, vol. 1, No. 1, 2004, 67-86.
Frith, P. et al., "Oxitropium Bromide, Dose-Response and Time-Response Study of a New Anticholinergic Bronchodilator Drug," Chest, 1986, 89 (2), 249-253.
Fuhr et al., "Efficacy and Safety of Twice-Daily Aclidinium Bromide 400 μg Compared with Placebo and Tiotropium 18 μg QD in Moderate to Severe COPD Patients," Chest, 138(4_Meeting Abstracts): 465A; Oct. 2010.
Gao, SH et al., Stereochemistry of the heterocyclic alcohols containing piperdine unit, Gaodeng Xuexiao Huaxue Xuebao, vol. 20: p. 232-236 (1999). (English Abstract).
Gavalda, A. et al., "Aclidinium Bromide, A Novel Long-Acting Muscarinic Antagonist for COPD with Improved Preclinical Renal and Urinary Safety Profile," Life Sciences, 2012, 90, 301-305.
Gavalda, A. et al., "Aclidinium Bromide, A Novel Muscamic Receptor Antagonist Combining Long Residence at M3 Receptors and Rapid Plasma Clearance," Poster Presentation at the European Respiratory Society Annual Congress in Stockholm, Sweden, 2007, 2 pages.
Gibson, et al., "The inhibitory profile of Ibudilast against the human phosphodiesterase enzyme family," Eur. J. of Pharmacology, 538: 39-42 (2006).
Global Initiative for Asthma, Global Strategy for Asthma Management and Prevention, NIH Publication No. 02-3659, Issued Jan. 1995, revised 2002.
Global Initiative for Chronic Obstructive Lung Disease, Global Strategy for the Diagnosis, Management, and Prevention of Chronic Obstructive Pulmonary Disease, National Institutes of Health, National Heart, Lung, and Blood Institute, Publication No. 2701, Mar. 2001.
Godoviko, et al., "Synthesis and Muscarinolytic Activity of Quinuclidinyl Benzylate Iodoalkylates," Pharmceutical Chemistry Journal, vol. 19, No. 9, 602-604 (1985).
Gras, J. et al., "Aclidinium Bromide, A Novel Long-Acting Anticholinergic Drug, Has a Good Preclinical Cardiovascular Safety Profile," Published as a Poster Presentation at European Respiratory Society Annual Congress in Berlin, Germany, 2008, 2 pages.
Gras, J. et al., "The Preclinical Urinary and Renal Safety Profile of Aclidinium Bromide, A Novel Long-Acting Anticholinergic Drug," European Respiratory Society Meeting in Berlin, 2008, 1 page.
Greenburg and Goss, "Therapies for Insomnia and Comorbid Chronic Obstructive Pulmonary Disease with a Focus on Ramelteon (Rozerem)," P&T, 34(9): 502-508 (2009).
Grob, CA et al., "Die Synthese von 4-Brom- und 4-Hydroxy-Chinuclidin," Helv. Chim. Acta 41: 1184-1191 (1958).
Gross, N. et al., "Dose Response to Ipratropium as a Nebulized Solution in Patients with Chronic Obstructive Pulmonary Disease, A Three-Center Study," American Review of Respiratory Disease, 1989, 139, 1188-1191.
Gross, N J. et al., "Efficacy and safety of formoterol fumarate delivered by nebulization to COPD patients", Repiratory Medicine, vol. 102, 2008, pp. 189-197.
Gross, N. et al., "Inhalation by Nebulization of Albuterol-Ipratropium Combination (Dey Combination) Is Superior to Either Agent Alone in the Treatment of Chronic Obstructive Pulmonary Disease," Respiration, 1998, 65, 354-362.
Gross, N. et al., "Role of the Parasympathetic System in Airway Obstruction Due to Emphysema," New England Journal of Medicine, 1984, 16 311 (7), 421-425.
Hancox, RJ et al., "Randomised trial of an inhaled B2 agonist, inhaled corticosteroids and their combination in the treatment of asthma," Thorax, 54: 482-487 (1999).
Hansel, T. et al., Eds., An Atlas of Chronic Obstructive Pulmonary Disease, COPD, The Parthenon Publishing Group, London, 2004, ISBN 1-84214-004-3, pp. 85-89, 103, 136, 139, 140, 151-156, 168-170, 210-212.
Hansel, T. et al., Eds., New Drugs for Asthma, Allergy and COPD, Progress in Respiratory Research, Karger, Basel, 2001, 31, ISBN 3805568622, Selection Titled: Current Therapy for Asthma by P. J. Barnes, pp. 6-10.
Hardman, J. et al.. Eds., Goodman and Gilman's: The Pharmacological Basis of Therapeutics, Ninth Edition, McGraw-Hill, New York, 1996, Chapter 28: Drugs Used in the Treatment of Asthma by W. Serafin, pp. 659-682.
Hardman, J. et al., Eds., Goodman and Gilman's: The Pharmacological Basis of Therapeutics, Tenth Edition, McGraw-Hill, New York, 2001, ISBN 0-07-135469-7, Chapter 10: Catecholamines, Sympathomimetic Drugs, and Adrenergic Receptor Antagonists by B. B. Hoffman, pp. 215-232.
Hardman, J. et al., Eds., Goodman and Gilman's: The Pharmacological Basis of Therapeutics, Tenth Edition, McGraw-Hill, New York, 2001, ISBN 0-07-135469-7, Chapter 28: Drugs Used in the Treatment of Asthma by B.J. Undem et al., pp. 733-754.
Hardman, J. et al., Eds., Goodman and Gilman's: The Pharmacological Basis of Therapeutics, Tenth Edition, McGraw-Hill, New York, 2001, ISBN 0-07-135469-7, Chapter 3: Principles of Therapeutics by A.S. Nies, pp. 45-66.
Hardman, J. et al., Eds., Goodman and Gilman's: The Pharmacological Basis of Therapeutics, Tenth Edition, McGraw-Hill, New York, 2001, ISBN 0-07-135469-7, Chapter 7: Muscarinic Receptor Agonists and Antagonists by J.H. Brown et al., pp. 155-173.
Heacock, RA et al., "Materials and Methods," The Annals of Applied Biology, Marsh RW and Thomas, I, eds, Cambirdge at the University Press, vol. 46, pp. 356-366 (1958).
Hele, D., "New Approaches to the Modulation of Inflammatory Processes in Airway Disease Models: ATS, May 18-23, 2001, San Francisco," Respiratory Research, 2001, 2 (5), E003, 4 pages.
Huang, et al., "Preferential inhibition of human phosphodiesterase 4 by ibudilast," Life Sciences, 78:2663-2668 (2006).
India Patent No. 244472, Opposition Affidavit of Dr. S. G. Deshpande, dated Jun. 5, 2012, 17 pages.
Instructions for Medicine, The Merck Manual, M., "MIR", 1997, vol. 2, p. 693. (English translation also attached).
International Search Report and Written Opinion of the ISR/EP for International Application No. PCT/EP2008/000782 dated Apr. 8, 2008, 12 pages.

(56) References Cited

OTHER PUBLICATIONS

International Search Report for International Application No. PCT/EP2009/001831, dated Jul. 2, 2010.
International Search Report for International Application No. PCT/EP2009/001832, dated Jul. 5, 2010.
International Search Report dated Nov. 15, 2007, for International Application No. PCT/EP2007/006278 (WO 2008/009397 A1).
International Search Report of International Application No. PCT/EP2013/060808, dated Jul. 16, 2013.
International Search Report of International Application No. PCT/EP2013/076606, dated Jun. 26, 2014.
International Search Report of International Application No. PCT/EP2012/056575, dated Jun. 4, 2012.
Interview Summary dated Mar. 12, 2014, in U.S. Appl. No. 12/528,267.
Introduction to Pharmacology, 2003, pp. 96 and 181-188.
Johnson, M. "Beta2-Andrenoreceptors Mechanisms of Action of Beta2-Agonists," Pediatric Respiratory Reviews, 2001, 2, 57-62.
Johnson, M., "Salmeterol," Medicinal Research Reviews, 1995, 15 (3), 225-257.
Joos, G. et al., "Bronchodilator effects of aclidinium bromide, a novel long-acting anticholinergic, in COPD patients: a phase II study," Abstract from European Respiratory Society dated Sep. 16, 2007.
Joos, G. et al., "Bronchodilatory Effects of Aclidinium Bromide, A Long-Acting Muscarinic Antagonist in COPD Patients," Respiratory Medicine, 2010, 104, 865-872.
Joos Poster "Bronchodilator effects of aclidinium bromide, a novel long-acting anticholinergic, in COPD patients: a phase II study," presented at the Annual Congress of the European Respiratory Society (ERS) in Stockholm, Sweden, 2007; Enlarged Figures 2(a), 2(b) and 3 of poster, 3 pages.
Joos GF et al., Poster "Bronchodilator effects of aclidinium bromide, a novel long-acting anticholinergic, in COPD patients: a phase II study," presented at the Annual Congress of the European Respiratory Society (ERS) in Stockholm, Sweden, 2007, 4 pages.
Joos GF et al., Poster presented at the Annual Congress of the European Respiratory Society (ERS) in Stockholm, Sweden, 2007; Printout of the ERS webpage relating to the presention, 2 pages.
Judgment by the High Court of Justice, Chancery Division, Patents Court, Claim No. HC 07 CO 2104 Between Laboratories Almirall, S.A. and Boehringer Ingelheim International GmbH, 2009.
Katzung, B., Ed., Basic and Clinical Pharmacology, Eighth Edition, McGraw-Hill, New York, 2001, ISBN 0-8385-0598-8, Chapter 20: Drugs used in Asthma by H.A. Boushey, pp. 333-349.
Khan, S. et al., "Effect of the Long-Acting Tachykinin NK1 Receptor Antagonist MEN 11467 on Tracheal Mucus Secretion in Allergic Ferrets," British Journal of Pharmacology, 2001, 132 (1), 189-196.
Konzett, H. et al., "Versuchsanordnung zu Untersuchungnen an der Bronchialmuskulatur," Arch. Exp. Path. Pharmacol. 195: 71-74(1940).
Korean Patent Application No. 2009-7017243, Notice of Preliminary Rejection issued Jan. 29, 2014 and English translation (10 pages).
Kreese, H., "Almirall: Slowly Moving Forward with Aclidinium Bromide," Oct. 15, 2008, article available at: http://www.pharmaceutical-business-review.com, 1 page.
Kuca, K. et al., "A General Method for the Quatemization of N,N-Dimethyl Benzylamines with Long Chain N-Alkylbromides," Journal of Applied Biomedicine, 2004, 2, 195-198.
Kumar, R. et al., "Inhibition of Inflammation and Remodeling by Roflumilast and Dexamethasone in Murine Chronic Asthma," The Journal of Pharmacology and Experimental Therapeutics, 2003, 307, 349-355.
Kumazawa, T et al., "Inhibitors of Acyl-CoA Cholesterol Acyltransferase 1. Synthesis and Hypocholesterolemic Activity of Dibenz[b,e]oxepin-11carboxanilides," J. Med. Chem 37(6): 804-810 (1994).

*Laboratories Almirall, S.A. v. Boehringer Ingelheim International GmbH* (2009) EWHC (CH) (Patent) HC 07 CO 2104 (Eng.) (Unpublished); Declaration from Dr. Ramon Basser confirming the availability of D2 and D3, dated Dec. 13, 2007.
*Laboratories Almirall, S.A. v. Boehringer Ingelheim International GmbH* (2009) EWHC (CH) (Patent) HC 07 CO 2104 (Eng.) (Unpublished); First Expert Report of Clive Peter Page dated Oct. 3, 2008.
*Laboratories Almirall, S.A. v. Boehringer Ingelheim International GmbH* (2009) EWHC (CH) (Patent) HC 07 CO 2104 (Eng.) (Unpublished); First Expert Report of John Francis Costello dated Oct. 3, 2008.
*Laboratories Almirall, S.A. v. Boehringer Ingelheim International GmbH* (2009) EWHC (CH) (Patent) HC 07 CO 2104 (Eng.) (Unpublished); First Expert Report of Professor Johan Zaagsma dated Sep. 30, 2008, statistical analysis of 90-180 minute timeframe, calculation of confidence interval for differences between AUC of measured effects of the combination and calculated sum (p value) according to (b) and (c) method analysis; and heart rate data.
*Laboratories Almirall, S.A. v. Boehringer Ingelheim International GmbH* (2009) EWHC (CH) (Patent) HC 07 CO 2104 (Eng.) (Unpublished); First Expert Report of Professor Peter John Barnes, dated Sep. 29, 2008.
*Laboratories Almirall, S.A. v. Boehringer Ingelheim International GmbH* (2009) EWHC (CH) (Patent) HC 07 CO 2104 (Eng.) (Unpublished); Opponent's Experimental Report 2.
*Laboratories Almirall, S.A. v. Boehringer Ingelheim International GmbH* (2009) EWHC (CH) (Patent) HC 07 CO 2104 (Eng.) (Unpublished); Second Expert Report of Clive Peter Page dated Oct. 27, 2008, and statistical analysis of Boehringer Experiment.
*Laboratories Almirall, S.A. v. Boehringer Ingelheim International GmbH* (2009) EWHC (CH) (Patent) HC 07 CO 2104 (Eng.) (Unpublished); Second Expert Report of John Francis Costello dated Oct. 23, 2008.
*Laboratories Almirall, S.A. v. Boehringer Ingelheim International GmbH* (2009) EWHC (CH) (Patent) HC 07 CO 2104 (Eng.) (Unpublished); Second Expert Report of Professor Peter John Barnes dated Oct. 27, 2008.
*Laboratories Almirall, S.A. v. Boehringer Ingelheim International GmbH* (2009) EWHC (CH) (Patent) HC 07 CO 2104 (Eng.) (Unpublished); Third Expert Report of Clive Peter Page dated Nov. 7, 2008.
*Laboratories Almirall, S.A. v. Boehringer Ingelheim International GmbH* (2009) EWHC (CH) (Patent) HC 07 CO 2104 (Eng.) (Unpublished); Witness Statement of Ramon Basser dated Oct. 1, 2008.
*Laboratories Almirall, S.A. v. Boehringer Ingelheim International GmbH* (2009) EWHC (CH) (Patent) HC 07 CO 2104 (Eng.) (Unpublished); Third Expert Report of Professor Johan Zaagsma dated Nov. 4, 2008.
*Laboratories Almirall, S.A. v. Boehringer Ingelheim International GmbH* (2009) EWHC (CH) (Patent) HC 07 CO 2104 (Eng.) (Unpublished); Opponent's Experimental Report 1.
*Laboratories Almirall, S.A. v. Boehringer Ingelheim International GmbH* (2009) EWHC (CH) (Patent) HC 07 CO 2104 (Eng.) (Unpublished); Second Expert Report of Professor Johan Zaagsma dated Oct. 27, 2008.
*Laboratories Almirall, S.A. v. Boehringer Ingelheim International GmbH* (2009) EWHC (CH) (Patent) HC 07 CO 2104 (Eng.) (Unpublished); Witness Statement of Thierry Benoit Bouyssou, dated Sep. 30, 2008.
*Laboratories Almirall, S.A. v. Boehringer Ingelheim International GmbH* (2009) EWHC (CH) (Patent) HC 07 CO 2014 (Eng.) (Unpublished); Claimant's Notice of Experiments in Reply.
*Laboratories Almirall, S.A. v. Boehringer Ingelheim International GmbH EWHC* (CH) (Patent) HC 07 CO 2104 (English); English High Court Judgment (2009).
Larsson, L et al., "The Hydrogen Bond Condition in Some Anticholinergic Esters of Glycolic Acids I," Acta. Pharma. Suec. 11(3): 304-308 (1974).
Le Souef, P, "The meaning of lung dose", Allergy, vol. 54, 1999, pp. 93-96.

(56) References Cited

OTHER PUBLICATIONS

Letter dated Jun. 6, 2008, from Powell Gilbert LLP to Bristows regarding HC07 C02104, 6 pages.
Lopez-Vidiero, M. et al., "Effect of Atropine on Sputum Production," Thorax, 1975, 30, 543547.
Lötvall, J. et al. "Similar bronchodilation with formoterol delivered by Aerolizer or Turbuhaler", Can Respir J., vol. 6, No. 5., Oct. 1999, pp. 412-416.
Lu, S. et al., "An Oral Selective M3 Cholinergic Receptor Antagonist in COPD," Eur Respir J. 28:772-780 (2006).
Lund, H. et al., "Quaternization Reactions," Acta Chemica Scandinavica, 1973, 27, 383-390.
Lygo, B. et al., "Asymmetric Approaches to 2-Hydroxymethylquinuclidine Derivatives," Tetrahedron, 1999, 55, 2795-2810.
Maesen, F.P.V. et al., "Ba 679 Br, A New Long-Acting Antimuscarinic Bronchodilator: A Pilot Dose-Escalation Study in COPD," European Respiratory Journal, 1993, 6, 1031-1036.
Magnussen, H. et al., "Peak inspiratory flow through the Genuair® inhaler in patients with moderate or severe COPD," Respiratory medicine, Bailliere Tindall, London, GB, vol. 103, No. 12, pp. 1832-1837 (2009).
Maltais et al., "Aclidinium bromide improves exercise endurance and lung hyperinflation in patients with moderate to severe COPD," Respiratory Medicine, vol. 105, No. 4, pp. 580-587 (2011) (Abstract).
Martin, L. "Drugs for Asthma/COPD—A Medical Primer for Physicians," http://www/lakesidepress.com/pulmonary/Asthma-Rx.html (updated Feb. 1999).
Martin et al. "Effect of Ipratropium Bromide Treatment on Oxygen Saturation and Sleep Quality in COPD," Chest, 1999; 115:1338-1345.
Martindale, The Complete Drug Reference, Kathleen Parfitt ed., 32nd ed., pp. 745-747 (1999).
Mashkovskiy, M.D., Medicaments, Moscow, Navaya Volna, 2001, p. 11.
Matera, M. et al., "Ultra-Long-Acting 2-Adrenoceptor Agonists," Drugs, 2007,67 (4), 503-515.
May, EL et al. "Studies in the Anthracene Series V. A Novel Rearrangement in the Reaction of Halomethyl Ketones with Secondary Amines," J. Am. Chem. Soc. 70: 1077-1079 (1948).
McNicholas, et al., "Long-acting inhaled anticholinergic therapy improves sleeping oxygen saturation in COPD," Eur Respir J, 23: 825-831; (2004).
Medical Dictionary, Edited by Ishiyaku Shuppan KK, 2001, p. 1554.
Merck Manual Home Edition article titled "Severe Acute Respiratory (SARS)," 2 pages, accessed Jul. 11, 2007.
Merck Manual Home Edition articles titled "Bronchopulmonary Dysplasia (BPD)," 2 pages; "Langerhans' Cell Granulomatosis," 2 pages; "Respiratory Tract Infections," 3 pages; "Pulmonary Embolism," 5 pages; and "Lung Cancer" 5 pages; accessed May 14, 2007.
Merck Manual of Diagnosis and Therapy, Robert Berkow ed., 16th Edition, p. 646-657 (1992).
Merck Manual, "Chronic Obstructive Airway Disorders," 17th Edition, p. 565 (1999).
Mery, P-F. et al., "Muscarinic Regulation of the L-Type Calcium Current in Isolated Cardiac Myocytes," Life Sciences, 1997,60(13-14), 1113-1120.
Meyers, AI et al., "Resolution of a-Substituted Mandelic Acids via Chiral Oxazolines Using Pressurized Chromatography," J. Org. Chem. 45(14): 2912-2914 (1980).
Mikhailov, I.B., Desk Book of the Physician for clinical pharmacology, St. Petersburg, 2001, pp. 424-425, 428, 439-440.
Mintzer, J. et al., "Anticholinergic Side-Effects of Drugs in Elderly People," Journal of the Royal Society of Medicine, 2000, 93 (9), 457-462.
Miralpeix, M. et al., "Assessment of the potency and duration of action of aclidinium bromide in guinea pig isolated trachea in vitro"; Eur Respir J., vol. 30 , 2007, pp. 354s-357s, Abstract P2159.
Miralpeix, M. et. al., "The Inhaled Anticholinergic Agent, Aclidinium Bromide, Reverses Cholinergic-Induced Bronchoconstriction in Guinea Pigs with a Fast Onset of Action and a Long Duration of Effect," Published as a Poster Presentation at the European Respiratory Society Annual Congress, Berlin, Germany, 2008 (2 pages).
Molfino, "Drugs in Clinical Development for Chronic Obstructive Pulmonary Disease"; Respiration, vol. 72, No. I, 2005, pp. 105-112.
Montero, J. et al., "Effect of Aclidinium Bromide, A Novel Long-Acting Anticholinergic, on Salivation, Colonic Motility and Faecal Output in Different Animal Models," European Respiratory Society Meeting in Berlin, 2008, 1 page.
Murray, J. et al., Eds., Textbook of Respiratory Medicine, Third Edition, W.B. Saunders Company, Philadelphia, 2000, ISBN 0-7216-7711-8, Chapter 10: Respiratory Pharmacology by P.J. Barnes, pp. 231, 232, 252-265.
Murray, J. et al., Eds., Textbook of Respiratory Medicine, Third Edition, W.B. Saunders Company, Philadelphia, 2000, ISBN 0-7216-7711-8, Chapter 11: Airway Pharmacology by P. J. Barnes, pp. 267-296.
Murray, J. et al., Eds., Textbook of Respiratory Medicine, Third Edition, W.B. Saunders Company, Philadelphia, 2000, ISBN 0-7216-7711-8, Chapter 38: Chronic Bronchitis and Emphysema by C.A. Piquette, pp. 1187-1245.
Murray, J. et al., Eds., Textbook of Respiratory Medicine, Third Edition, W.B. Saunders Company, Philadelphia, 2000, ISBN 0-7216-7711-8, Chapters 11 and 38, pp. 267-296 and 1187-1245.
Murray, J. et al., Eds., Textbook of Respiratory Medicine, Third Edition, W.B. Saunders Company, Philadelphia, 2000, ISBN 0-7216-7711-8, Chapter 39: Asthma by H.A. Boushey et al., pp. 1247-1289.
National Sleep Foundation, "COPD and Difficulty Breathing," http:/www.sleepfoundatIon.org/article/sleep-related-problems/chronic-obstructive-pulmonarydisease-and-sleep, (2009).
National Sleep Foundation, "Asthma and Sleep," http://www.sleepfoundation.org/article/sleep-topics/asthmaand sleep, (2011).
Nishikawa, M. et al., "Effect of Short- and Long-Acting 2-Adrenoceptor Agonists on Pulmonary 2-Adrenoceptor Expression in Human Lung," European Journal of Pharmacology, 1996,318, 123-129.
Nishimura, et al., "Additive effect of oxitropium bromide in combination with inhaled corticosteroids in the treatment of elderly patients with chronic asthma," Allerology International 48: 85-88 (1999).
Noronha-Blob, L et al., Stereoselective antimuscarininc effects of 3-quinuclidinyl atrolactate and 3-quinuclidinyl xanthene-9-carboxylate, European Journal of Pharmacology 211:97-103 (1992).
Notice of Allowance dated Aug. 16, 2015, in U.S. Appl. No. 13/672,893.
Notice of Allowance dated Dec. 21, 2005 in U.S. Appl. No. 11/116,777.
Notice of Allowance dated Feb. 26, 2010, in U.S. Appl. No. 12/074,929.
Notice of Allowance dated Jan. 10, 2011 in U.S. Appl. No. 12/787,772.
Notice of Allowance dated Jan. 9, 2007 in U.S. Appl. No. 11/324,919.
Notice of Allowance dated Jun. 23, 2011 in U.S. Appl. No. 12/374,185.
Notice of Allowance dated Mar. 30, 2005 in U.S. Appl. No. 10/740,264.
Notice of Allowance dated Nov. 23, 2007 in U.S. Appl. No. 11/636,181.
Notice of Allowance dated Oct. 20, 2011 in U.S. Appl. No. 13/011,131.
Notice of Allowance dated Sep. 13, 2006 in U.S. Appl. No. 11/325,059.
Notification of the Preliminary Research Report for FR 0505473, dated Dec. 12, 2005, 5 pages.
Notification of the Research Report for BE 200500268, dated Nov. 3, 2005, 5 pages.
Notification of the Transmittal of the International Search Report and the Written Opinion of the International Searching Authority, or

(56) References Cited

OTHER PUBLICATIONS the Declaration for International Application No. PCT/EP2005/005836 dated Aug. 10, 2005, 14 pages.
Notification of the Transmittal of the International Search Report and the Written Opinion of the International Searching Authority, or the Declaration for International Application No. PCT/EP2005/005837 dated Aug. 4, 2005, 14 pages.
Notification of the Transmittal of the International Search Report and the Written Opinion of the International Searching Authority, or the Declaration for International Application No. PCT/EP2005/005838 dated Aug. 17, 2005, 14 pages.
Notification of the Transmittal of the International Search Report and the Written Opinion of the International Searching Authority, or the Declaration for International Application No. PCT/EP2005/005839 dated Aug. 5, 2005, 14 pages.
Notification of the Transmittal of the International Search Report and the Written Opinion of the International Searching Authority, or the Declaration for International Application No. PCT/EP2005/005840 dated Aug. 17, 2005, 14 pages.
Notification of the Transmittal of the International Search Report and the Written Opinion of the International Searching Authority, or the Declaration for International Application No. PCT/EP2005/005841 dated Aug. 8, 2005, 14 pages.
Nyberg, K. et al., "Investigations of Dithienylglycolic Esters," Acta. Chem. Scand. 24: 1590-1596 (1970).
Office Action dated Apr. 15, 2011 in U.S. Appl. No. 13/011,131.
Office Action dated Apr. 18, 2013, in U.S. Appl. No. 13/672,893.
Office Action dated Apr. 22, 2004 in U.S. Appl. No. 10/740,264.
Office Action dated Apr. 28, 2006 in U.S. Appl. No. 11/324,919.
Office Action dated Apr. 2, 2015, in U.S. Appl. No. 14/111,211.
Office Action dated Aug. 18, 2016, in U.S. Appl. No. 15/218,391.
Office Action dated Aug. 24, 2015, in U.S. Appl. No. 13/692,032.
Office Action dated Dec. 13, 2011 in U.S. Appl. No. 12/921,892.
Office Action dated Dec. 30, 2014, in U.S. Appl. No. 13/692,032.
Office Action dated Jan. 26, 2012 in U.S. Appl. No. 12/921,921.
Office Action dated Jan. 29, 2014, in U.S. Appl. No. 13/672,893.
Office Action dated Jan. 29, 2016, in U.S. Appl. No. 14/652,817.
Office Action dated Jul. 16, 2013, in U.S. Appl. No. 13/672,893.
Office Action dated Jul. 22, 2004 in U.S. Appl. No. 10/740,264.
Office Action dated Jul. 6, 2007 in U.S. Appl. No. 11/636,181.
Office Action dated Jun. 2, 2014, in U.S. Appl. No. 13/692,032.
Office Action dated Jun. 4, 2012, in U.S. Appl. No. 12/921,921.
Office Action dated Jun. 6, 2014, in U.S. Appl. No. 12/528,267.
Office Action dated Mar. 13, 2012, in U.S. Appl. No. 12/528,267.
Office Action dated Mar. 14, 2006 in U.S. Appl. No. 11/325,059.
Office Action dated Mar. 4, 2009 in U.S. Appl. No. 12/074,929.
Office Action dated May 11, 2012 in U.S. Appl. No. 12/921,892.
Office Action dated May 20, 2016, in U.S. Appl. No. 13/692,032.
Office Action dated Nov. 24, 2015, in U.S. Appl. No. 14/111,211.
Office Action dated Oct. 13, 2010, in U.S. Appl. No. 12/374,185.
Office Action dated Oct. 19, 2010, in U.S. Appl. No. 12/787,772.
Office Action dated Oct. 2, 2007 in U.S. Appl. No. 10/892,033.
Office Action dated Oct. 6, 2014, in U.S. Appl. No. 13/672,893.
Office Action dated Oct. 7, 2009 in U.S. Appl. No. 12/074,929.
Office Action dated Sep. 19, 2005 in U.S. Appl. No. 11/116,777.
Office Action dated Sep. 23, 2013 in U.S. Appl. No. 12/528,267.
Office Action dated Sep. 28, 2011, in U.S. Appl. No. 12/528,267.
Office Action dated Jul. 20, 2016, in U.S. Appl. No. 14/403,220.
Page, C. et al., Integrated Pharmacology, Second Edition, Mosby, Edinburgh, 2002, ISBN 0 7234 3221 X, Chapter 19: Drugs and the Pulmonary System.
Parfitt, K., Ed., Martindale: The Complete Drug Reference, Thirty-Second Edition, 1999, 745-747.
Peretto, I. et al., "Medicinal Chemistry and Therapeutic Potential of Muscarinic M3 Antagonists," Medicinal Research Reviews, 2009, published online in Wiley InterScience, DOI 10.1002/med.20158, 36 pages.
Pharmacology Manual, Edited by KK Nanzando, 2002, pp. 20 and 23.
Pokrzywinski, RF et al. "Development and psychometric assessment of the COPD and Asthma Sleep Impact Scale (OASIS)," Health and Quality of Life Outcomes, 2009, 7:98.
Prat et al; "Discovery of Novel Quaternary Ammonium Derivatives of (3R)-Quinuclidinol Esters as Potent and Long-acting Muscarinic Antagonists with Potential for Minimal Systemic Exposure after Inhaled Administration . . . "; J Med Chem; Aug. 27, 2009; 52(16), pp. 5076-5092.
Puddicombe, S. et al., "Involvement of the Epidermal Growth Factor Receptor in Epithelial Repair in Asthma," The FASEB Journal, 2000, 14, 1362-1374.
Rabe, et al., "Roflumilast—an oral anti-inflammatory treatment for chronic obstructive pulmonary disease: a randomized controlled trial," Lancet, 366: 563-571 (Aug. 13, 2005).
Rang, H et al., Eds., Pharmacology, Third Edition, 1995, Chapter 17, "The Respiratory System," pp. 351-366.
Rang, HP et al., "Pharmacology," Churchill Livingston Inc., pp. 358-361 (1995).
Rees, PJ "Bronchodilators in the therapy of chronic obstructive pulmonary disease," Eur. Respir. Mon. 7:135-149 (1998).
Rennard, SI, (1997) "Anticholinergics and beta2-agonists: Efficacy, Safety and Combination Therapy in Chronic Obstructive Pulmonary Disease," Chapter 9, Barnes and Buist (Ed.) The Role of Anticholinergics in Chronic Obstructive Pulmonary Disease and Chronic Asthma, pp. 137-144, Gardiner-Caldwell Communications Limited.
Restriction Requirement dated Jan. 28, 2014, in U.S. Appl. No. 13/692,032.
Restriction Requirement dated Apr. 7, 2016, in U.S. Appl. No. 14/561,857.
Restriction Requirement dated Jan. 25, 2016, in U.S. Appl. No. 14/403,220.
Rigaudy, J et al., "Cetones Derivees du Dibzeno [a,d]cycloheptadiene. La Dibenzo-2,3-6,7 Cycloheptadienedione-4,5" Bull. Soc. Chim. France, 638-643 (1959).
Ringdahl, R. et al., "Facile Preparation of the Enantiomers of 3-Acetoxyquinuclidinol," Acta Pharm Suec. 16: 281-283 (1979).
Rochester, C., Ed., Clinics in Chest Medicine, W.B. Saunders Company, Philadelphia, 2000, 21 (4), ISSN 0272-5231, Selection Titled: Update on Pharmacologic Therapy for Chronic Obstructive Pulmonary Disease by G. Ferguson, pp. 723-738.
Romain, O. et al., "Actualites Pharmaceutiques," (2006) 1596-1598, 13(12), XP027997707, ISSN: 0929-693X, DOI:10.1016/J.ARCPED.2006.09.019, Archives De Pediatrie, Elsevier, Paris, FR.
Rucinski, T. et al., Reuters, "Almirall Seen Likely to Repeat Lung Drug Trial," Oct. 14, 2008, article available at: http://money.aol.ca/article/almirall-seen-likely -to-repeat-lung-drug- tria/379398, 1 page.
Rzeszotarski, W. et al., "Affinity and Selectivity of the Optical Isomers of 3-Quinuclidinyl Benzilate and Related Muscarinic Antagonists," Journal of Medicinal Chemistry, 1988, 31, 1463-1466.
Schelfhout, V. et al., "Activity of LAS 34273, A New Long Acting Anticholinergic Antagonist, in COPD Patients," American Thoracic Society, 2003, 99th International Conference, Abstract No. A319.
Schelfhout, V. et al., "Activity of LAS 34273, A New Long Acting Anticholinergic Antagonist, in COPD Patients," Poster, ATS 2003—99th International Conference, May 2003 and Expanded Version, 4 pages.
Schelfhout, V. et al., "Activity of LAS 34273, A New Long Acting Anticholinergic Antagonist," American Thoracic Society, 2003, 99th International Conference, Abstract No. A93.
Schelfhout, V. et al., "Activity of LAS 34273, A New Long Acting Anticholinergic Antagonist," Poster, ATS 2003—99th International Conference, May 2003 and Expanded Version, 4 pages.
Schelfhout, VJ et al., Activity of LAS 34273, A New Long Acting Anticholinergic Antagonist, in COPD Patients, poster, ATS 2003—99th International Conference, May 2003.
Schelfhout, VJ et al., "Activity of LAS 34273, a new long acting anticholinergic antagonist," ATS 2003—99th International Conference, May 2004.

(56) References Cited

OTHER PUBLICATIONS

Schelfhout, V et al., "Bronchodilator/bronchoprotective effects of aclidinium bromide, a novel long-acting anticholinergic: a phase I study", Eur Respir J., vol. 30, 2007; pp. 354s-357s, Abstract P2146.
Schmidt, R. "Dose-Finding Studies in Clinical Drug Development," Eur J Clin PHarmacol. 1988. 34:15-19.
Search Report for Application No. CY 3405, Date of completion of the search Jun. 28, 2006, 5 pages.
Search Report for Patent Application No. 1029151, dated Feb. 14, 2006, 5 pages.
Sentellas et al; "Aclidinium Bromide, a New, Long-acting, Inhaled Muscarinic Antagonist: in vitro Plasma Inactivation and Pharmacological Activity of its Main Metabolites"; Eur J Pharm Sci.; Mar. 18, 2010; 1 page Abstract Only.
Sentellas, S. et al., "Aclidinium Bromide, A New, Long-Acting, Inhaled Muscarinic Antagonist: In vitro Plasma Inactivation and Pharmacological Activity of Its Main Metabolites," European Journal of Pharmaceutical Sciences, 2010, 39, 283-290.
Serafin, W. "Drugs Used in the Treatment of Asthma," Goodman A Gilman's The Pharmacological Basis of Therapeutics, Chapter 28, Joel G. Hardman et al eds, 9th Edition, pp. 659-682 (1996).
Sestanj, K. "A Facile Formation of Dibenzo[a,b] cycloheptenylium Ion by Decarbonylation Color Reactions of the Cyheptaminde Metabolites," Can. J. Chem. 49: 664-665 (1971).
Sharma, V. et al. "Does Mammalian Heart Contain Only the M2-Muscarinic Receptor Subtype?," Life Sciences, 1997, 60 (13-14), 1023-1029.
Singh, D. et al., "A randomised, placebo- and active-controlled dose-finding study of aclidinium bromide administered twice a day in COPD patients," Pulm Pharmacol Ther (2012) 25(3) 2012 248-253.
Singh, D. et al., "A randomised, placebo- and active-controlled dose-finding study of aclidinium bromide administered twice a day in COPD patients," Pulm Pharmacol Ther. Apr. 2013;26(2):305. (Abstract Only).
Singh, D. et al., "Corrigendum to 'A randomised, placebo- and active-controlled dose-finding study of aclidinium bromide administered twice a day in COPD patients' [Pulm Pharmacol Ther 25(3) 2012 248-253]," Pulm Pharmacol Ther. Apr. 2013;26(2):305.
Spiriva Pharmacology Reviews, Part 1, 47 pages, http://www.accessdata.fda.gov/drugsatfda_docs/nda/2004/21-395_Spiriva.cfm, website last accessed Mar. 6, 2014.
Spiriva Pharmacology Reviews, Part 2, 47 pages, retrieved Jul. 31, 2015, from http://www.accessdata.fda.gov/drugsatfda_docs/nda/2004/21-395.pdf_Spiriva_Pharmr_P2.pdf.
Spiriva Pharmacology Reviews, Part 3, 47 pages, retrieved Jul. 31, 2015, from http://www.accessdata.fda.gov/drugsatfda_docs/nda/2004/21-395.pdf_Spiriva_Pharmr_P3.pdf.
Spiriva Pharmacology Reviews, Part 4, 47 pages, retrieved Jul. 31, 2015, from http://www.accessdata.fda.gov/drugsatfda_docs/nda/2004/21-395.pdf_Spiriva_Pharmr_P4.pd.
Spiriva Pharmacology Reviews, Part 5, 47 pages, retrieved Jul. 31, 2015, from http://www.accessdata.fda.gov/drugsatfda_docs/nda/2004/21-395.pdf_Spiriva_Pharmr_P5.pdf.
Spiriva Pharmacology Reviews, Part 6, 46 pages, retrieved Jul. 31, 2015, from http://www.accessdata.fda.gov/drugsatfda_docs/nda/2004/21-395.pdf_Spiriva_Pharmr_P6.pdf.
Spirva® HandHihaler® Prescribing Information, Boehringer Ingelheim International GmbH, 59873/US/2, Sep. 2004.
Spitzer, W. et al., "The Use of P-Agonists and the Risk of Death and Near Death from Asthma," New England Journal of Medicine, 1992, 326, 501-506.
Steckel, H. et al., "Functionality testing of inhalation grade lactose", European Journal of Pharmaceutics and Biopharmacetuics, vol. 57, 2004, 495-505.
Suissa, S. et al., "Patterns of Increasing P-Agonist Use and the Risk of Fatal or Near-Fatal Asthma," European Respiratory Journal, 1994, 7, 1602-1609.
Summary of Product Characteristics (SmPC) for "Duaklir Genuair 340 micrograms/12 micrograms inhalation powder", 35 pages.
Summary of Product Characteristics (SmPC) for "Eklira Genuair 322 micrograms inhalation powder", 36 pages.
Tavakkoli et al., "Drug Treatment of Asthma in the 1990s, Achievements and New Strategies," Drugs, 57(1): 1-8 (1999).
Teixera et al., "Phosphodiesterase (PDE) 4 inhibitors: anti-inflammatory drugs of the future," TiPS, 18:164 (May 1997).
Telko, M J et al., "Dry Powder Inhaler Formulation", Respiratory Care, vol. 50, No. 9, Sep. 2005, 1209-27.
Tennant, R. et al., "Long-Acting P2-Adrenoreceptor Agonists or Tiotropium Bromide for Patients with COPD: Is Combination Therapy Justified?," Current Opinion in Pharmacology, 2003, 3, 270-276.
The Merck Manual of Diagnosis and Therapy, Seventeenth Edition, 1999, Foreword and Chapter 68, "Chronic Obstructive Airway Disorders," pp. 555-583.
The Merck Manual, "Instructions for Medicine," 1997, 2, 693 and English-language translation (4 pages).
Theolair™ Prescribing Information, 3M Pharmaceuticals, 601000, May 1998, 12 pages.
Therapy in Chronic Obstructive Pulmonary Disease by S.I. Rennard et al., pp. 137-144.
Torphy, T. "Phosphodiesterase Isozymes, Molecular Targets for Novel Antiasthma Agents," Am. J. Respit. Crit. Care Med., 157:351-370 (1998).
Traunecker, W. et al., "Pharmacological Effects of a Combination of Fenoterol Hydrobromide and Ipratropium Bromide," Respiration, 1986, 50 (4), 244-251.
U.S: National Institute of Health, "A Trial Assessing LAS34273 in Moderate to Severe Stable Chronic Obstructive Pulmonary Disease (COPD)", updated Feb. 20, 2008, 2 pages. Available from: https://clinicaltrials.gov/archive/NCT00363896/2008_02_20.
U.S: National Institute of Health, "Efficacy and Safety of LAS34273 in Patients with Moderate to Severe Stable Chronic Obstructive Pulmonary Disease (COPD)", updated Feb. 20, 2008, 2 pages. Available from: https://clinicaltrials.gov/archive/NCT00358436/2008_02_20.
U.S. Appl. No. 10/891,552 Advisory Action mailed May 24, 2007, 4 pages.
U.S. Appl. No. 10/891,552 Amendment Under 37 C.F.R. § 1.111 in Response to Apr. 11, 2006, Office Action dated Sep. 19, 2006, 15 pages.
U.S. Appl. No. 10/891,552 Amendment Under 37 C.F.R. § 1.116 in Response to Dec. 12, 2006, Final Office Action dated May 7, 2007, 16 pages.
U.S. Appl. No. 10/891,552 Examiner-Initiated Interview Summary and Notice of Abandonment mailed Nov. 4, 2010, 4 pages.
U.S. Appl. No. 10/891,552 Final Office Action and Examiner-Initiated Interview Summary mailed Apr. 8, 2010, 30 pages.
U.S. Appl. No. 10/891,552 Final Office Action dated Dec. 12, 2006, 15 pages.
U.S. Appl. No. 10/891,552 Final Office Action dated Jan. 7, 2009, 26 pages.
U.S. Appl. No. 10/891,552 Interview Summary dated Apr. 22, 2008, 4 pages.
U.S. Appl. No. 10/891,552 Non-Final Office Action dated Apr. 11, 2006, 18 pages.
U.S. Appl. No. 10/891,552 Non-Final Office Action dated Aug. 22, 2007, 17 pages.
U.S. Appl. No. 10/891,552 Non-Final Office Action dated May 12, 2008, 21 pages.
U.S. Appl. No. 10/891,552 Non-Final Office Action dated Aug. 17, 2009, 26 pages.
U.S. Appl. No. 10/891,552 Reply for RCE Filing dated Jun. 8, 2009, 21 pages.
U.S. Appl. No. 10/891,552 Reply to May 24, 2007, Advisory Action dated Jun. 1, 2007, 4 pages.
U.S. Appl. No. 10/891,552 Reply to Office Action Under 37 C.F.R. §1.111 dated Feb. 22, 2008, 17 pages.
U.S. Appl. No. 10/891,552 Reply to Office Action Under 37 C.F.R. § 1.111 dated Oct. 13, 2008, 17 pages and Declaration of Thierry Benoit Bouyssou Under 37 C.F.R. § 1.132 dated Sep. 5, 2008, 6 pages.

(56) References Cited

OTHER PUBLICATIONS

U.S. Appl. No. 10/891,552 Reply to Office Action Under 37 C.F.R. §1.111 dated Jan. 19, 2010, 15 page.
U.S. Appl. No. 10/891,552 Supplemental Reply dated Jun. 24, 2009, 2 pages, and Declaration Under 37 C.F.R. § 1.132 dated Jun. 15, 2009, 6 pages.
U.S. Appl. No. 10/891,552 Supplemental Reply to Office Action dated Mar. 29, 2010, 15 pages.
U.S. Appl. No. 10/892,033 Advisory Action dated Jan. 31, 2012, 5 pages.
U.S. Appl. No. 10/892,033 Advisory Action dated Jun. 3, 2010, 4 pages.
U.S. Appl. No. 10/892,033 Applicant Initiated Interview Summary mailed Nov. 16, 2011, 3 pages.
U.S. Appl. No. 10/892,033 Brief on Appeal Under 37 C.F.R. §41.37 dated Apr. 7, 2012, 91 pages.
U.S. Appl. No. 10/892,033 Examiner Interview Summary Record dated Nov. 17, 2010, 3 pages.
U.S. Appl. No. 10/892,033 Examiner Interview Summary Record dated Feb. 2, 2011, 3 pages.
U.S. Appl. No. 10/892,033 Examiner's Answer to Appeal Brief mailed May 18, 2012, 26 pages.
U.S. Appl. No. 10/892,033 Final Office Action dated Mar. 2, 2009, 19 pages.
U.S. Appl. No. 10/892,033 Final Office Action dated Mar. 31, 2010, 18 pages.
U.S. Appl. No. 10/892,033 Final Office Action dated Sep. 19, 2011, 41 pages.
U.S. Appl. No. 10/892,033 Issue Fee dated Dec. 2, 2010, 3 pages.
U.S. Appl. No. 10/892,033 Issue Fee dated Oct. 26, 2010, 1 page.
U.S. Appl. No. 10/892,033 Non-Final Office Action dated Jul. 18, 2008, 18 pages.
U.S. Appl. No. 10/892,033 Non-Final Office Action dated Mar. 2, 2011, 32 pages.
U.S. Appl. No. 10/892,033 Non-Final Office Action dated Oct. 15, 2009, 18 pages.
U.S. Appl. No. 10/892,033 Notice of Abandonment dated Aug. 3, 2015, 3 pages.
U.S. Appl. No. 10/892,033 Notice of Allowance dated Nov. 22, 2010, 7 pages.
U.S. Appl. No. 10/892,033 Notice of Allowance dated Oct. 7, 2010, 9 pages.
U.S. Appl. No. 10/892,033 Notice of Withdrawal from Issue Branch mailed Jan. 10, 2011, 3 pages.
U.S. Appl. No. 10/892,033 Notice of Withdrawal from Issue Branch mailed Oct. 29, 2010, 1 page.
U.S. Appl. No. 10/892,033 Patent Board Decision, Appeal 2012-009895 issued May 19, 2015, 14 pages.
U.S. Appl. No. 10/892,033 Reply After Final Rejection dated Jan. 19, 2012, 18 pages.
U.S. Appl. No. 10/892,033 Reply After Final Rejection dated May 11, 2010, 10 pages.
U.S. Appl. No. 10/892,033 Reply Brief dated Jun. 21, 2012, 5 pages.
U.S. Appl. No. 10/892,033 Reply dated Dec. 18, 2008, 27 pages.
U.S. Appl. No. 10/892,033 Reply dated Jan. 13, 2010, 8 pages.
U.S. Appl. No. 10/892,033 Reply dated Jul. 5, 2011, 21 pages.
U.S. Appl. No. 10/892,033 Reply for RCE dated Aug. 3, 2009, 19 pages.
U.S. Appl. No. 10/892,033, Office Action Response dated Apr. 2, 2008, 18 pages.
U.S. Appl. No. 11/116,777, Amendment and Response to Office Action dated Sep. 30, 2005, 14 pages.
U.S. Appl. No. 11/409,157 Examiner Interview Summary Record issued Feb. 7, 2007, 3 pages.
U.S. Appl. No. 11/409,157 Requirement for Restriction/Election mailed Nov. 16, 2006, 10 pages.
U.S. Appl. No. 11/409,157 Response to Restriction Requirement dated May 16, 2007, 7 pages.
U.S. Appl. No. 12/070,298 Examiner Interview Summary Record mailed Apr. 7, 2011, 4 pages.
U.S. Appl. No. 12/875,601 Amendment Under 37 C.F.R. § 1.111 in Response to Jan. 26, 2015, Office Action filed Jun. 5, 2015, 19 pages.
U.S. Appl. No. 12/875,601 Interview Summary dated Jan. 27, 2011, 4 pages.
U.S. Appl. No. 12/875,601 Non-Final Office Action dated Jan. 26, 2015, 26 pages.
U.S. Appl. No. 12/875,601 Non-Final Office Action dated Apr. 4, 2014, 22 pages.
U.S. Appl. No. 12/875,601 Reply to Office Action Under 37 C.F.R. §1.111 dated Oct. 3, 2014, 15 pages, and Declaration of Thierry Benoit Bouyssou Under 37 C.F.R. § 1.132 dated Sep. 5, 2008, 6 pages, and Declaration Under 37 C.F.R. § 1.132 dated Jun. 15, 2009, 6 pages.
U.S. Appl. No. 12/912,145 Amendment and Response to Requirements for Restriction and Election of Species dated Dec. 4, 2013, 16 pages.
U.S. Appl. No. 12/912,145 Final Office Action dated Jul. 23, 2014, 54 pages.
U.S. Appl. No. 12/912,145 Non-Final Office Action dated Jan. 30, 2014, 40 pages.
U.S. Appl. No. 12/912,145 Notice of Abandonment dated Feb. 6, 2015, 3 pages.
U.S. Appl. No. 12/912,145 Reply dated Jun. 30, 2014, 14 pages.
U.S. Appl. No. 12/912,145 Requirement for Restriction/Election dated Nov. 4, 2013, 10 pages.
U.S. Appl. No. 13/354,873 Final Office Action dated Dec. 28, 2012, 4 pages.
U.S. Appl. No. 13/354,873 Non-Final Office Action dated Aug. 17, 2012, 8 pages.
U.S. Appl. No. 13/354,873 Notice of Allowance dated Apr. 11, 2013, 6 pages.
U.S. Appl. No. 13/939,742 Non-Final Office Action dated Sep. 6, 2013, 8 pages.
U.S. Appl. No. 13/939,742 Notice of Allowance dated Mar. 20, 2014, 8 pages.
U.S. Appl. No. 14/305,701 Applicant Initiated Interview Summary dated Jan. 22, 2016, 3 pages.
U.S. Appl. No. 14/305,701 Requirement for Restriction/Election dated Jul. 31, 2015, 5 pages.
U.S. Appl. No. 14/305,701 Response to Election of Species Requirement dated Feb. 1, 2016, 4 pages.
U.S. Appl. No. 14/311,102 Non-Final Office Action dated Jul. 25, 2014, 9 pages.
U.S. Appl. No. 14/311,102 Notice of Allowance dated Feb. 10, 2015, 7 pages.
U.S. Appl. No. 14/712,866 Non-Final Office Action dated Jun. 5, 2015, 9 pages.
U.S. Appl. No. 14/712,866 Notice of Allowance dated Jan. 6, 2016.
Ueda, I. "The Rearrangement of 10-Bromo-10,11-Dihydrodibenzo[b,f]thiepin-11-one and Related Compounds in an Alkaline Solution," Bulletin of the Chemical Society of Japan, 48(4): 2306-2309 (1975).
United States Pharmacopeia, pp. 242-263 (2013).
Van Gestel, Arnoldus J. et al., "Predicting daily Physical Activity in Patients with Chronic Obstructive Pulmonary Disease," PLoS One, vol. 7, Issue 11, p. e48081 (2012).
Van Noord, J. et al., "Comparison of Once Daily Tiotropium, Twice Daily Formoterol and the Free Combination, Once Daily, in Patients with COPD," Poster, ATS 2003—99th International Conference, May 2003, 1 page.
Van Noord, J. et al., "Tiotropium Maintenance Therapy in Patients with COPD and the 24-h Spirometric Benefit of Adding Once or Twice Daily Formoterol During 2-week Treatment Periods," Poster, ATS 2003—99th International Conference, May 2003, 1 page.
Virk, D., "Sleep disturbances in individuals diagnosed with respiratory diseases; asthma, bronchiectasis, COPD and asbestosis," European Journal of Neurology, vol. 17, No. Suppl. 3, p. 623 (2010).
Waelbroek, M. et al., "Binding of Selective Antagonists to Four Muscarinic Receptors (M1 to M4) in Rat Forebrain," Mol. Pharmacol. 38:267-273 (1990).

(56) References Cited

OTHER PUBLICATIONS

Walsh, D. et al., "Synthesis and Antiallergy Activity of 4-(Diarylhydroxymethyl)-1-[3-(aryloxy)propyl]piperidines and Structurally Related Compounds," Journal of Medicinal Chemistry, 1989, 32, 105-118.

Watz, H. et al., "Physical activity in patients with COPD," European Respiratory Journal, vol. 33, No. 2, pp. 262-272 (2009).

Wedzicha, J. et al., Eds., The Effective Management of Chronic Obstructive Pulmonary Disease, Aesculapius Medical Press, London, 2001, ISBN 0 903044 19 7, Chapter 3: The Importance of Achieving Diagnostic Accuracy by R.A. Stockley, pp. 21-30; Chapter 4: Current Thinking on the Nature of Exacerbation and the Time Course and Recovery of Exacerbations of COPD by J.A. Wedzicha et al., pp. 33-41.

Wedzicha, J. et al., Eds., The Effective Management of Chronic Obstructive Pulmonary Disease, Aesculapius Medical Press, London, 2001, ISBN 1 903044 19 7, Chapter 5: Scientific Evidence and Expert Clinical Opinion for the Selection and Use of Bronchodilators: Clinical Decision Making in the Individual Patient by P.S. Marino et al., pp. 43-63.

WHO Drug Information, "International Nonproprietary Names for Pharmacological Substances (INN), Recommended International Nonproprietary Names: List 57," 2007, 21 (1), 53-55.

Zaagsma, J. et al. "Muscarinic Control of Airway Function," Life Sciences, 1997, 60 (13-14), 1061-1068.

Zaagsma, J. et al., Eds., Muscarinic Receptors in Airways Disease, Birkhauser Verlag, Basel, 2001, ISBN 3-7643-5988-9, Chapter Titled: The Role of Anticholinergics in Asthma and COPD by K.R. Chapman, pp. 203-219.

ACLIDINIUM FOR USE IN IMPROVING THE QUALITY OF SLEEP IN RESPIRATORY PATIENTS

This application is a continuation of U.S. patent application Ser. No. 14/111,211, having a 35 U.S.C. §371(c) date of Dec. 23, 2013, which is a National Stage Entry of PCT/EP2012/056575, filed Apr. 11, 2012, which claims the benefit of U.S. Provisional Application No. 61/497,771, filed Jun. 16, 2011, and also claims priority to European Patent Application No. 11382114.4, filed Apr. 15, 2011, all of which are incorporated herein by reference.

FIELD OF THE INVENTION

The invention relates to a novel use of aclidinium, which can be advantageously used to improve the quality of sleep in respiratory patients.

BACKGROUND OF THE INVENTION

Respiratory diseases, such as asthma and chronic obstructive pulmonary disease (COPD), are a significant global health program, with an increasing incidence throughout the world. They are usually characterised by an inflammatory dysfunction of the airways which results in bronchoconstriction.

In asthma inflammation is driven by exposure to a variety of triggers, including allergens and viruses, which activate components of both the innate and acquired immune responses. In COPD inflammation occurs primarily because of exposure to noxious particles and gases, in particular to cigarette smoke. Rather than a single pathologic condition, COPD is a term encompassing several disorders, such as chronic bronchitis or emphysema.

Asthma and COPD are commonly associated with severe impairment of the physical functions as a consequence of pulmonary symptoms such as dyspnoea (breathlessness), fatigue, cough, wheezing, chest tightness or congestion, and sputum production. Many patients with respiratory diseases complain of the serious impact of these symptoms in the quality of their sleep.

In COPD patients, sleep-related complaints are the third most commonly reported symptoms, after dyspnoea and fatigue (Kinsman et al, Chest, 1983, 83, 755-761). In the case of asthma, 80% of the patients are woken at least occasionally by nocturnal wheeze and cough, and many patients with severe stable asthma are woken virtually every night (Turner-Warwick, M.; Am. J. Med., 1988, 85 (suppl. 1B), 6-8).

Sleep complaints frequently reported by respiratory patients are for example longer latency to falling asleep, difficulty in staying asleep, frequent arousals and awakenings, superficial sleep, reduction of total sleep time, waking up too early and not being able to get back to sleep, generalised insomnia and, overall, a much poorer quality of sleep. Excessive daytime sleepiness arid restricted physical activity during the day due to breathlessness in the morning are also common consequences of the impaired quality of sleep.

These sleep disturbances tend to be more severe with advancing disease and substantially reduce the quality of life of respiratory patients.

Bronchodilating agents like the beta-adrenergic agonists or the antagonists of cholinergic muscarinic receptors (commonly known as anticholinergics antimuscarinics) are usually prescribed for inhalation to respiratory patients suffering from obstructive airway diseases, such as asthma or COPD. commercially available antichohnergics are synthetic tropane derivatives, and include ipratropium, oxitropium, and tiotropium. Tiotropium, is the only long-acting anticholinergic currently on the market.

It is well known that the impact of the circadian rhythm on airway responsiveness and airway resistance is much larger in respiratory patients that in normal subjects. As a consequence, respiratory patients are particularly prone to bronchoconstriction at night and in the early morning hours and this is the main factor affecting the quality of their sleep. Therefore, a treatment aimed at overcoming or preventing bronchoconstriction during the night is highly desirable. However, a study by Calverley el al., in Thorax, 2003, 58 (10), 855-860 shows that the administration of the long-acting bronchodilator tiotropium in the evening does not produce more bronchodilation during the night than when it is administered only in the morning.

It has now surprisingly been found that aclidinium significantly diminishes the occurrence of the sleep disturbances commonly seen in respiratory patients, increasing thus quality of sleep and overall quality of life.

Aclidinium is 3(R)-(2-hydroxy-2,2-dithien-2-ylacetoxy)-1-(3-phenoxypropyl)-1-azoniabicyclo[2.2.2]octane, a long-acting muscarinic receptor antagonist in development by Almirall for administration by inhalation in the treatment of respiratory diseases, especially asthma and COPD. It was first disclosed in WO 01/04118.

Aclidinium is rapidly hydrolysed in human plasma to two inactive metabolites, and hence has a reduced potential for systemic side effects and a wider safety margin than currently available inhaled anticholinergic treatments. Its additional effect in improving quality of sleep is an unexpected finding of this invention.

SUMMARY AF THE INVENTION

The present invention provides aclidinium, or any of its stereoisomers or mixture of stereoisomers, or a pharmaceutically acceptable salt or solvate thereof, for use in improving the quality of sleep in respiratory patients.

Preferably, aclidinium is in the form of a salt with anion $X^-$. Most preferably, the anion $X^-$ is bromide.

In a preferred embodiment, the respiratory patient suffers from a disease selected from acute or chronic bronchitis, emphysema, asthma and chronic obstructive pulmonary disease, preferably asthma and chronic obstructive pulmonary disease, most preferably chronic obstructive pulmonary disease.

In another embodiment, aclidinium is administered as a pharmaceutical composition suitable for inhalation, preferably in the form of a dry powder. The composition can be administered by means of any inhaler device, more preferably the Genuair®.

Typically, a dry powder formulation comprises a pharmaceutically acceptable carrier selected from mono-, di- or polysaccharides and sugar alcohols. Preferably, the carrier is lactose.

Aclidinium is administered at least once a day, preferably in the morning or in the evening. More preferably aclidinium is administered twice daily. In a most preferred embodiment aclidinium is administered twice daily, one in the morning and another one in the evening.

The effective dose of aclidinium to be used per inhalation is the equivalent to a metered nominal dose from 100 to 1000 micrograms of aclidinium bromide in a dry powder for inhalation, more preferably 200 or 400 micrograms of aclidinium bromide.

In another preferred embodiment, aclidinium is co-administered with an additional medication suitable for the treatment of respiratory diseases, selected for example from one or more of the following: corticosteroids, beta-adrenergic agonists, PDE4 inhibitors, antihistamines, anti-1gE antibodies, leukotriene D4 inhibitors, inhibitors of egfr-kinase, p38 kinase inhibitors and/or NK1-receptor antagonists. The additional medications can be present in the same pharmaceutical composition as aclidinium or in separate pharmaceutical compositions. Preferably, the additional medication is selected from corticosteroids, beta-adrenergic agonists and/or PDE4 inhibitors.

The improvement by aclidinium of the quality of sleep of the respiratory patient can be measured by observing the reduction of one or more of the following:
a) Latency to falling asleep
b) Total number of awakenings
b) Early awakenings
c) Difficulty in staying asleep
d) Superficial sleep
e) Insomnia
f) Daytime sleepiness or fatigue
g) Restriction of activities during the morning
and/or by the increase of total sleep time.

Among the clinical factors that may contribute to the improvement of the quality of sleep by aclidinium are reductions in one or more of the following respiratory complaints during sleep time:
a) Cough severity and/or frequency
b) Sputum production
c) Wheezing
d) Chest tightness
e) Chest congestion
f) Bronchoconstriction
g) Breathlessness
h) Need of rescue medication The invention further provides a pharmaceutical composition comprising aclidinium for improving the quality of sleep in respiratory patients.

The invention further provides the use of aclidinium in the manufacture of a medicament for improving the quality of sleep in respiratory patients.

The invention further provides a method of improving the quality of sleep in respiratory patients, which method comprises administering to said patient an effective amount of aclidinium, as defined above.

DETAILED DESCRIPTION OF THE INVENTION

Typically, the aclidinium is administered in the form of a salt with an anion $X^-$, wherein $X^-$ is a pharmaceutically acceptable anion of a mono or polyvalent acid. More typically, $X^-$ is an anion derived from an inorganic acid, such as hydrochloric acid, hydrobromic acid, sulphuric acid and phosphoric acid, or an organic acid such as methanesulphonic acid, acetic acid, fumaric acid, succinic acid, lactic acid, citric acid or maleic acid. Most preferably the aclidinium is in the form of aclidinium bromide.

The compound of the invention may exist in both unsolvated and solvated forms. The term solvate is used herein to describe a molecular complex comprising a compound of the invention and an amount of one or more pharmaceutically acceptable solvent molecules. The term hydrate is employed when said solvent is water. Examples of solvate forms include, but are not limited to, compounds of the invention in association with water, acetone, dichloromethane, 2-propanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate.

The words "treatment" and "treating" are to be understood as embracing amelioration of symptoms of a disease or condition and/or elimination or reduction of the cause of the disease or condition and/or prevention of the appearance of the disease or its symptoms.

The term "therapeutically effective amount" refers to an amount sufficient to effect treatment when administered to a patient in need of treatment.

Aclidinium can also be used in combination with other drugs known to be effective in the treatment of the diseases or the disorders indicated above, For example aclidinium can be combined with corticosteroids or glucocorticoids, beta-adrenergic agonists, PDE4 inhibitors, antihistamines, anti-IGE antibodies, leukotriene D4 antagonists, inhibitors of egfr kinase, p38 kinase inhibitors and/or NK-1 receptor agonists.

Corticosteroids that can be combined with aclidinium in the present invention particularly include those suitable for administration by inhalation in the treatment of respiratory diseases or conditions, e.g., prednisolone, methylprednisolone, dexarnethasone, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, deprodone propionate, fluticasone propionate, halobetasol propionate, loteprednol etabonate, betamethasone butyrate propionate, flunisolide, prednisone, dexamethasone sodium phosphate, triamcinolone, betatnethasone 17-valerate, betamethasone, betamethasone dipropionate, hydrocortisone acetate, hydrocortisone sodium succinate, prednisolone sodium phosphate and hydrocortisone probutate. Budesonide and mometasone are especially preferred.

Beta-adrenergic agonists that can be combined with aclidinium in the present invention particularly include β2 adrenergic agonists useful for treatment of respiratory diseases or conditions, for example, selected from the group consisting of arformoterol, bambuterol, bitolterol, broxaterol carbuterol, clenbuterol, dopexamine, fenoterol, formoterol, hexoprenaline, ibuterol, isoprenaline, mabuterol, meluadrine, nolomirole, orciprenaline, pirbuterol, procaterol, reproterol, ritodrine, rimoterol, salbutatnol, salmeterol, sibenadet, sulfonterol, terbutaline, tulobuterol, vilanterol, olodaterol, KUL-1248, LAS-100977, carmoterol and indacaterol, in free or pharmaceutically acceptable salt form. Preferably, the β2 adrenergic agonist is a long-acting β2 adrenergic agonist, e.g., selected from the group consisting of formoterol, salmeterol, carmoterol, vilanterol, olodaterol, LAS-100977 and indacaterol in free or pharmaceutically acceptable salt form.

PDE4 inhibitors that can be combined with aclidinium in the present invention include denbufylline, rolipram, cipamfylline, arofylline, filaminast, piclamilast, mesopram, drotaverine hydrochloride, lirimilast, roflumilast, cilomilast, 6-[2-(3,4-Diethoxyphenyl)thiazol-4-yl]pyridine-2-carboxylic acid, (R)-(+)-4-[2-(3-Cyclopentyloxy-4-methoxyphenyl)-2-phenylethyl]pyridine, N-(3,5-Dichloro-4-pyridinyl)-2-[1-(4-fluorobenzyl)-5-hydroxy-1H-indol-3-yl]-2-oxoacetamide, 9-(2-Fluorobenzyl)-N6-methyl-2-(trifluoromethyl)adenine, N-(3,5-Dichloro-4-pyridinyl)-8-methoxyquinoline-5-carboxamide, N-[9-Methyl-4-oxo-1-phenyl-3,4,6,7-tetrahydropyrrolo[3,2,1-jk][1,4]benzodiazepin-3(R)-yl]pyridine-4-carboxamide, 3-[3-(Cyclopentyloxy)-4-methoxybenzyl]-6-(ethylamino)-8-isopropyl-3H-purine hydrochloride, 4-[6,7-Diethoxy-2,3-bis(hydroxymethyl)naphthalen-1-yl]-1-(2-methoxyethyl)pyridin-2(1H)-one, 2-carbomethoxy-4-cyano-4-(3-cyclopropylmethoxy-4-difluoromethoxyphenyl)cyclohexan1-one, cis [4-cyano-4-(3-cyclopropylmethoxy-4-difluoromethoxyphenyl)cyclohexan-1-ol, ONO-6126 (Eur Respir J 2003, 22(Suppl. 45): Abst 2557) and the compounds claimed in the PCT patent application number WO03/097613, and PCT/EP03/14722 and in the Spanish patent application numer P200302613.

Aclidinium for use in the present invention may be administered by any suitable route to provide local antimuscarinic action. It is preferably administered by inhalation, e.g., as a powder, spray, or aerosol, preferably as a dry powder. Pharmaceutical compositions comprising aclidinium may be prepared using conventional diluents or excipients and techniques known in the galenic art.

Medicaments for administration in a dry powder the inhalation desirably have a controlled particle size. The optimum particle size for inhalation into the bronchial system is usually 1-10 µm, preferably 2-5 µm. Particles having a size above 20 µm are generally too large when inhaled to reach the small airways. To achieve these particle sizes the particles of the active ingredient as produced may be size reduced by conventional means, e.g. by micronisation or supercritical fluid techniques. The desired fraction may be separated out by air classification or sieving. Preferably, the particles will be crystalline.

Achieving a high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient, for example a mono-, di- or polysaccharide or sugar alcohol, such as lactose, mannitol or glucose is generally employed. The particle size of the excipient will usually he much greater than the inhaled medicament within the present invention. When the excipient is lactose it will typically be present as lactose particles, preferably crystalline alpha lactose monohydrate, e.g, having an average particle size range of 20-1000 µm, preferably in the range of 90-150 µm. In one embodiment, the lactose particles for use in formulations of the invention have a d10 of 90-160 µm, a d50 of 170-270 µm, and d90 of 290-400 µm.

Suitable lactose materials for use in the present invention are commercially available, e.g., from DMW Internacional (Respitose GR-001, Respitose SV-001, Respitose SV-003); Meggie (Capsulac 60, Inhalac 70, Capsulac 60 INH); and Borculo Domo (Lactohale 100-200, Lactohale 200-300, and Lactohale 100-300).

The ratio between the lactose particles and the aclidinium by weight will depend on the inhaler device used, but is typically, e.g., 5:1 to 200:1, for example 50:1 to 150:1, e.g., 60-70:1.

In a preferred embodiment, the aclidinium is administered in the form of a dry powder formulation of aclidinium bromide in admixture with lactose, in a ratio by weight of aclidinium to lactose of 1:50 to 1:150, suitable for administration via a dry powder inhaler, wherein the aclidinium particles have an average particle size of from 2 to 5 µm in diameter, e.g., less than 3 µm in diameter, and the lactose particles have have a d10 of 90-160 µm, a d50 of 170-270 µm, and d90 of 290-400 µm.

Dry powder compositions for topical delivery to the lung by inhalation may, for example, be presented in capsules and cartridges of for example gelatine or blisters of for example laminated aluminium foil, for use in an inhaler or insufflator. Each capsule or cartridge may generally contain between 0.001-50 mg, more preferably 0.01-5 mg of active ingredient or the equivalent amount of a pharmaceutically acceptable salt thereof Alternatively, the active ingredient (s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices, Aclidinium is preferably administered with a multi-dose inhaler, more preferably with the Genuair®(formerly known as Novolizer SD2FL), which is described the following patent applications Nos: WO97/000703, WO03/000325 and WO2006/008027.

Dosages will vary depending on, e.g., the individual, the mode and frequency of administration, and the nature and severity of the condition to be treated, Daily dosages for a 70 kg adult human may typically for example be on the order of 100-1000 micrograms of active agent in the form of dry powder for inhalation.

EXAMPLE 1

In a Phase IIa randomized, double-blind, crossover trial, patients with moderate to severe COPD received aclidinium 400 micrograms twice-daily (in the morning, 9 am, and in the evening, 9 pm) and placebo for 15 days, with a 9-15 day washout between treatment periods.

Sleep quality was assessed with daily records on a patient diary card using a 0-4 score according to the following criteria:

| | |
|---|---|
| 0 | No awakenings |
| 1 | Early awakening or awakening once during the night |
| 2 | Early awakening or awakening two or more times during the night |
| 3 | Awakening for most time during the night |
| 4 | The patient could not sleep at all |

Patients treated with aclidinium showed a significantly improved quality of sleep compared to untreated patients.

EXAMPLE 2

In a double-blind, randomised, placebo-controlled Phase III trial, the quality of sleep and the use of rescue medication was assessed during twice-daily treatment of aclidinium bromide in COPD patients.

COPD patients with FEV1/FVC<70% were randomised (1:1:1) to aclidinium 200 micrograms, 400 micrograms, or placebo. The quality of sleep was reported daily using electronic diaries and a questionnaire, which assessed symptom frequency and severity and its effect on morning activities. Rescue medication use was also assessed.

At Week 12, aclidinium significantly improved the quality of sleep compared to placebo. Aclidinium 200 mcg and 400 mcg significantly reduced the severity of breathlessness and cough at night, the frequency of awakenings and the difficulty to fall back sleep. Additionally, the production of sputum and the use of rescue medication were also reduced.

Both aclidinium doses also significantly reduced the severity of early morning breathlessness and the impact of breathlessness and cough on morning activities.

EXAMPLE 3

In a Phase IIa randomised, double-blind, double-dummy, crossover trial, patients with moderate-to-severe COPD received inhaled aclidinium 400 µg BID, tiotropium 18 µg QD and placebo for 15 days, with a 9-15 day washout between treatment periods.

The incidence of sleep difficulties was recorded daily on a patient diary card. As in Example 1, the scores ranged from 0 for none to 1-4 for increasing severity of the sleep difficulties. The change in the score produced by each treatment with respect to the baseline was then measured.

The average score (+/−SEM) of the patients treated with tiotropium was −0.011 (0.091), which is practically identical to the baseline and very similar to the score of 0.061 (0.088), observed in the patients treated with placebo. There is no statistically significant difference between these two scores (p>0.05). In contrast, the score of the patients treated with aclidinium was −0.123 (0.089). In this case there is a statistically significant difference with placebo (p<0.05).

These phase IIa results demonstrate that the remarkable improvement of sleep quality produced by aclidinium is not observed when the patients are treated with tiotropium, the reference anticholinergic drug currently in the market. This unexpected effect of aclidinium is therefore not obvious and involves an inventive step.

The invention claimed is:

1. A method for improving the quality of sleep in a respiratory patient experiencing sleep disturbances, comprising:
   administering to the patient a pharmaceutical composition comprising aclidinium or any of its stereoisomers or mixture of stereoisomers, or a pharmaceutically acceptable salt or solvate thereof.

2. The method according to claim 1, wherein the aclidinium is in the form of aclidinium bromide.

3. The method according to claim 1, wherein the respiratory patient suffers from asthma or chronic obstructive pulmonary disease (COPD).

4. The method according to claim 1, wherein the aclidinium is in the form of a dry powder formulation suitable for inhalation.

5. The method for use in a dry powder formulation according to claim 4, providing a metered nominal dose of aclidinium equivalent to from 100 to 1000 micrograms of aclidinium bromide per inhalation.

6. The method according to claim 5, wherein the metered nominal dose of aclidinium is equivalent to 200 micrograms of aclidinium bromide per inhalation.

7. The method according to claim 5, wherein the metered nominal dose of aclidinium is equivalent to 400 micrograms of aclidinium bromide per inhalation.

8. The method according to claim 1, wherein aclidinium is administered at least once per day.

9. The method according to claim 8, wherein aclidinium is administered twice daily.

10. The method according to claim 1, wherein aclidinium is co-administered with a therapeutically effective amount of at least one other medication chosen from corticosteroids, beta-adrenergic agonists, and PDE4 inhibitors.

11. The method according to claim 1, wherein the quality of sleep is improved by reducing at least one of the following sleep disturbances:
   a) latency to falling asleep;
   b) total number of awakenings;
   c) early awakenings;
   d) difficulty in staying asleep;
   e) superficial sleep;
   f) insomnia;
   g) daytime sleepiness or fatigue;
   h) restriction of activities during the morning;
   and/or by increasing total sleep time.

12. The method according to claim 1, wherein the pharmaceutical composition comprises aclidinium in an effective amount of aclidinium.

13. The method according to claim 1, wherein the patient suffers from a respiratory disorder and wherein the patient suffers from impaired sleep caused by sleep disturbances.

14. The method according to claim 13, wherein the patient suffers from asthma or chronic obstructive pulmonary disease.

15. The method according to claim 5, wherein the formulation is administered in a dosage comprising an amount of aclidinium ranging from 200 micrograms to 400 micrograms of aclidinium bromide per inhalation.

* * * * *